(12) United States Patent
Kuvshinov et al.

(10) Patent No.: US 7,790,950 B2
(45) Date of Patent: Sep. 7, 2010

(54) USE OF PHYTOENE SYNTHASE FOR CONTROLLING TRANSGENE ESCAPE

(76) Inventors: Viktor Kuvshinov, Aarteenetsijantie 4 F 54, Helsinki (FI) 00970; Kimmo Koivu, Riihikalllionkuja 8, Itasalmi (FI) 01100; Anne Kanerva, Riihikalllionkuja 8, Itasalmi (FI) 01100; Andrei Anissimov, Tilanhoitajankaari 4 A 26, Helsinki (FI) 00790

( * ) Notice: Subject to any disclaimer, the term of this patent is extended or adjusted under 35 U.S.C. 154(b) by 716 days.

(21) Appl. No.: 11/632,397

(22) PCT Filed: Jul. 5, 2005

(86) PCT No.: PCT/FI2005/050268

§ 371 (c)(1),
(2), (4) Date: Jan. 12, 2007

(87) PCT Pub. No.: WO2006/005807

PCT Pub. Date: Jan. 19, 2006

(65) Prior Publication Data

US 2008/0085996 A1    Apr. 10, 2008

Related U.S. Application Data

(63) Continuation-in-part of application No. 10/892,513, filed on Jul. 15, 2004, now Pat. No. 7,495,148, which is a continuation-in-part of application No. 09/617,543, filed on Jul. 14, 2000, now Pat. No. 6,849,776.

(51) Int. Cl.
*C12N 15/82* (2006.01)
*C12N 15/31* (2006.01)
*C12N 15/52* (2006.01)
*A01N 45/02* (2006.01)

(52) U.S. Cl. .................. 800/278; 800/287; 800/288; 536/23.2; 536/23.7; 536/24.1; 514/23; 514/53

(58) Field of Classification Search ................ None
See application file for complete search history.

(56) References Cited

U.S. PATENT DOCUMENTS

2002/0053095 A1    5/2002    Brown et al.

FOREIGN PATENT DOCUMENTS

| WO | WO9744465 | 11/1997 |
| WO | WO0206498 | 1/2002 |
| WO | WO03076633 | 9/2003 |

OTHER PUBLICATIONS

Shewmaker et al. The Plant Journal 20(4): 401-412 (Nov. 1999).*
Lindgren et al. Plant Physiology 132(2): 779-785 (Jun. 2003).*
Kuvshinov V. et al. Molecular control of transgene escape from genetically modified plants. Plant Sci. 2001 (160): 517-522.
Kuvshinov V. et al. Double recoverable block of function—a molecular . . . Environ. Biosafety Res 49 103-112 (2005).

* cited by examiner

*Primary Examiner*—David T Fox
(74) *Attorney, Agent, or Firm*—Dodds & Associates; Leea S. Somersalo; John Dodds

(57) ABSTRACT

The present invention is related to a recoverable block of function (RBF) system for controlling transgene escape and transgene containment in plants. The RBF-system comprises at least one blocking construct (BC), wherein the BC comprises as the blocking gene a nucleotide sequence or crtB gene encoding phytoene synthase, which is used alone or in combination with other BCs. The crtB gene expresses under the control of a germination specific promoter or a promoter constitutively repressed by a Recovering construct (RC) and blocks the germination of a transgenic seed. The blocked germination is recoverable by a user controlled intervention including addition of an effective amount of gibberellin and sugar and may involve so called recovering constructs (RCs), wherein the recovering gene may encode ent-copalyl diphosphate synthase or ent-kaurene synthase.

9 Claims, 13 Drawing Sheets

CrtB.F1 primer (SEQ ID NO:2)
　　*Hind*III　　*Nco*I　　*Esp*3I
atgaagcttatccatggatcgtctcacATGGCTGTTGG CTCGAAAAGTTTTGCGACTGC

Fig. 2A

CrtB.R1 primer (SEQ ID NO:3)
　　*Bam*HI　　*Nhe*I　　*Sac*I
catggatccatgctagcatgagctcgaCTAAATCGGGCGCTGCCAGAGATGGGCAGGGCG

Fig. 2B

Tps.F1 primer (SEQ ID NO:5)

AATCCGCCGCAGTGGCTCCATTCGGCGGCCTCAAATCCATGACTGGATTCCCAGTGAAGAA

Fig. 3A

Tps.R1 primer (SEQ ID NO:6)

CCACCATTGCTTGTAATGGAAGTAATGTCAGTGTTGACCTTCTTCACTGGGAATCCAGTCATGG

Fig. 3B

Tps.F2 primer (SEQ ID NO:7)

ATATCCTCTTCCGCTGTGACAACAGTCAGCCGTGCCTCTAGGGGGCAATCCGCCGCAGTGGCT

Fig. 3C

Tps.R2 primer (SEQ ID NO:8)

*GAAGAGAAGGGTTGTTCAT*GCACTTTACTCTTCCACCATTGCTTGTAATGG

Fig. 3D

Tps.F3 primer (SEQ ID NO:9)

*Xba*I    *Nco*I
gctatctagagcgccATGGCTTCTATGATATCCTCTTCCGCTGTGACAACAGT

Fig. 3E

Tps.R3 primer (SEQ ID NO:10)

*Bam*HI   *Nco*I
cgatggatccgcgccat*GGTCTCAACAGCATGGTTAAGAAGAGAAGGGTTGTTCA*

Fig. 3F

USE OF PHYTOENE SYNTHASE FOR CONTROLLING TRANSGENE ESCAPE

This is a submission to enter the national stage under 35 U.S.C. section 371. The international application WO2006/005807 was filed on 07 May 2005 as PCT/FI05/50268 and has been published on Jan. 19, 2006. The international application is a continuation-in-part of U.S. national application Ser. No. 10/892,513 filed 15th Jul. 2004, now U.S. Pat. No. 7,495,148, which is a continuation-in-part of U.S. application Ser. No. 09/617,543 filed 14th Jul. 2000, now U.S. Pat. No. 6,849,776.

SEQUENCE LISTING

A Sequence Listing according to 37 C.F.R. section 1.181 (c) is attached. Attached hereto is a diskette containing the Sequence Listing in computer readable form in accordance with 37 C.F.R. section 1.821 (e).

TECHNICAL FIELD OF THE INVENTION

The present invention is related to phytoene synthase for controlling transgene escape. A nucleotide sequence encoding phytoene synthase is used as a blocking gene in a Recoverable Block of Function (RBF) system, which comprises one or more blocking constructs (BCs), and means for recovering the blocked functions with or without one or more recovering constructs (RCs).

BACKGROUND OF THE INVENTION

The techniques of plant biotechnology have improved during the last ten years so that most of the crop species, which are of importance to mankind, can be routinely transformed. The industry seeks for new traits not only for agricultural or nutritional purposes, but also for pharmaceutical purposes. There is an increasing interest to develop efficient and economic production systems for useful biological compounds. Transgenic plants play an important role in the research aiming to develop such a system. Given the concerns of environmental impacts of genetically modified crops this development has clearly created a need for a reliable system to prevent transgene flow among crops and in their relatives. Accordingly, several research groups around the world are currently engaged in developing techniques for gene containment in transgenic crops.

The technologies that are aimed to prevent transgene flow can be categorized into one-component and two-component technologies. The main feature of the one-component systems is a factor, which enables a negative selection of transgenes from plant populations. As examples, the known concepts of male sterility, chloroplast transformation or 'Terminator' technology, are mentioned. One-component systems decrease gene flow, but they do not always provide a completely reliable containment. Two-factor technologies were developed in order to improve the gene containment. These systems use negative selection factors together with a recovering (rescuing or repairing) factor. The negative selection factors are usually lethal for the plant and therefore they totally prevent the transgene flow. The rescuing factor represses the action of the negative selection factor, disrupts its function or recovers the functions blocked by the negative selection factor. Examples of two-factor technologies are the systems described in the International patent publications WO 94/03619 (Bright et al.) and WO 00/37660 (Fabijanski et al.).

The International patent publication WO 02/064801 (Kuvshinov et al.) describes a two-factor system, where an excision construct (EC) is linked to the transgene of interest (TGI). The EC excises the whole insert from the genome of the host organism under natural conditions. An artificially activated repression construct represses the action of the EC and saves the transgenic insert in the host genome. This system removes the entire transgene insert and leaves the host genome free from the foreign genes. Thus, in natural conditions transgenic plant produces non-transgenic seeds only and can not produce transgenic seeds.

According to Gressel, Trends Biotechnol., 17, 361-366, 1999, inactivation of negative selection factor (gene) may happen with a frequency of approximately $10^{-6}$. In practice this means once during a growth season, in each middle sized field plot. Such a frequency of gene escape from a field, where the transgenic crop is cultivated for production of a vaccine or other pharmaceutical compounds would create public concerns. It has been suggested that the inactivation problem may be solved by using an one-component concept called mitigation tandem technique. In this technique the desired transgene is coupled in tandem with gene(s) that would render hybrid offspring or volunteer weeds less able to compete with crops, weeds and wild species. Examples of features that could be used in mitigation technique are secondary dormancy and dwarfing. A problem encountered with the tandem mitigation technique is that due to absence of a recovering system, removal of transgene from the population demands several generations. Therefore this technique does not provide sufficiently reliable transgene containment. The scarce sources of genes capable of mitigating, is another limitation of the technology.

The International patent publication WO 02/06498 corresponding to the US patent applications U.S. Ser. No. 10/892, 513, U.S. Ser. No. 10/644,664 and U.S. Ser. No. 09/617,543 (Kuvshinov et al.) all disclose a two-factor system called RBF-system (recoverable block of function system), which comprises at least one blocking construct (BC), which is an insert consisting of a blocking gene, which is linked to a transgene of interest (TGI), which is a gene encoding a desired protein or gene product, and at least one recovering construct (RC). According to said disclosure the BC(s) block(s) a vital physiological or molecular function of the host plant through developmental or organ specific expression. The RC is induced by an externally controllable stimulus and when induced it recovers the function previously blocked by expression of the BC(s).

Due to the increasing use of transgenic plants, not only new methods for controlling transgene escape in plants are needed, but also alternative new blocking genes, which may block essential functions of the plant particularly during germination and which can be recovered by a user controlled intervention.

Phytoene synthase is an enzyme in the biosynthetic pathway (FIG. 1) leading to production of carotenoids, which are biologically important in many organisms ranging from bacteria and fungi to higher plants.

Phytoene synthase produces phytoene (C40) from geranylgeranyl diphosphate (C20), which is a mutual precursor of carotenoids, tocopherols, gibberellins and chlorophyll (Fray et al., Plant J., 8, 693-701, 1995; Shewmaker et al., Plant J., 20, 401-412, 1999; Sandmann, Trends in Plant Sci., 6, 14-17, 2001). Bacterial crtB genes encoding phytoene synthase have been expressed in plants in order to increase content of carotenoids. "Golden" Rice (*Oryza sativa*) is an example of a transgenic plant seed overexpressing the phytoene synthase (Beyer et al., J. Nutr., 132, 505S-510S, 2002).

Seed-specific expression of the gene encoding phytoene synthase leads to a 50-fold increase in carotenoids, decrease in chlorophyll levels and slight delay of seed germination in *Brassica napus* (Shewmaker et al., Plant J., 20, 401-412, 1999). In tomato (*Lycopersicon esculentum*), constitutive expression of the crtB gene under 35S promoter results in a decreased level of chlorophyll and dwarfism, which was provoked by 30-fold reduction in levels of gibberellin (GA) (Fray et al., Plant J., 8, 693-701, 1995).

Embryo specific overexpression of plant endogenous phytoene synthase results in increased levels of carotenoids in seeds of *Arabidopsis* (Lindgren et al., Plant Physiol., 132, 779-785, 2003). The plant derived phytoene synthase increases the level of chlorophyll, whereas the level of α-carotene is only slightly increased. The plant derived phytoene synthase also results in decreased levels of gibberellins, whereas an increased level of abscisic acid (ABA) leads to delayed germination, which is not recoverable by a gibberellin addition.

Even if it is known that constitutive, seed or embryo specific overexpression of phytoene synthase delays seed germination, the gene encoding phytoene synthase does not totally prevent germination, because expression does not occur during germination. Because germination is delayed and not fully blocked, the seedlings are capable of overcoming the lack of gibberellins and excess of ABA. Accordingly, the constitutive, seed and embryo specific expression of crtB gene is not suitable for developing RBF-systems for controlling of transgene escape.

SUMMARY OF THE INVENTION

The present invention is related to the use of a nucleotide sequence encoding phytoene synthase for controlling transgene flow or transgene escape in plants. The nucleotide sequence encoding phytoene synthase is used as a blocking gene in a RBF-system, which comprises one or more BCs as well as means for recovering the blocked functions with or without one or more RCs.

Accordingly, the RBF-system is a combination of expression cassettes. The BC is an expression cassette or a plasmid, which can be inserted into the plant cell or plant tissue. In the present invention the BC comprises as a blocking gene at least one nucleotide sequence encoding phytoene synthase, which preferably expresses under the control of a germination specific promoter or a promoter constitutively repressed by an RC. The nucleotide sequence encoding phytoene synthase is an isolated, unmodified native crtB gene, which is obtainable from suitable available sources, such as plants, bacteria and fungi. Said nucleotide sequence may be artificially modified by truncation or synthetic means by adapting the crtB sequence to plant codon preference, for example by increasing the GC-content or AT-content.

The expression of the blocking or crtB gene preferably takes place under the control of a germination specific promoter, such as a sulfhydryl (or cysteine) endopeptidase (SH-EP) promoter or a Heat Shock (HS) promoter and prevents the transgenic plant seeds to germinate beyond the stage of cotyledon expansion.

The user controlled intervention comprises recovery of the blocked function by chemical or physical means. When the blocking gene is crtB, the recovery of the blocked germination is achieved by adding an effective amount of gibberellin or gibberellic acid and carbohydrates or sugar, particularly sucrose, into the growth medium during the germination phase. The effective amount is an amount that effectively recovers the blocked germination.

The RBF-system may be an one-insert system as the so called simple RBF-system, which comprises only the blocking crtB gene, which expresses under the control of a germination specific promoter and means for recovering the blocked germination. More complicated RBF-systems may be constructed comprising the BCs, RCs with respective TGIs, promoters and markers in one insert, as in a so called double blocking system, which comprise one or more BCs flanking one or more RCs and the TGI, or alternatively a site for inserting the TGI, or in two separate inserts as in a so called segregating RBF-system or delayed RBF-system, in which the BCs comprising a crtB gene and RCs are introduced into the plant separately one by one.

When two BCs are used in an RBF-system, they may contain two identical or similar or totally different crtB genes. CrtB genes with varying degrees of similarity or differences are obtainable by modifying crtB genes, which may be isolated from the same source. The modification is achieved, for example by artificial modification, preferably by modifying to plant codon preference, which may include, for example, an enriched GC-content or AT-content. CrtB genes with varying degrees of similarity and differences may be obtained by isolating the CrtB genes from different sources, for example from plant, bacterial or fungal sources. Nucleotide sequences comprising the full length or truncated CrtB genes may be used. If a truncated CrtB gene is used the prerequisite is that the truncated sequence still has the capacity of encoding phytoene synthase and blocking the germination.

The RBF-system may comprise two totally different BCs. One BC may comprise a crtB gene, which is recovered as defined in the present invention. The other BC may comprise a totally different blocking gene, for example, a gene encoding Barnase, which may be recovered by a gene encoding Barstar.

The RBF-system may in addition to the user controlled intervention contain one or more RCs. The RC is an expression cassette, vector or a plasmid, which may be inserted into the plant in the same insert as the BC (one-insert system) or in a separate insert (a two-insert system). The RC comprises a recovering gene, which may express for example a repressor polypeptide, which binds to the promoter(s) of the blocking gene. Thereby, the recovering gene inhibits the functions of the expression products (phytoene and/or barnase) of the blocking gene after induction of RC, which may be regulated by an inducible promoter, such as a heat shock inducible promoter.

Alternatively, the RC may comprise a nucleotide sequence, which encodes an enzyme involved in the synthesis of metabolites, which due to the overexpression of phytoene synthase have been depleted in the transgenic plant. Such nucleotide sequences are the sequences encoding the enzymes ent-copalyl diphosphate synthase or ent-kaurene synthase, which enzymes are needed for the synthesis of certain metabolites in the gibberellin biosynthetic pathway shown in FIG. 1.

BRIEF DESCRIPTION OF THE DRAWINGS

FIG. 2A depicts CrtB.F1 forward primer sequence (SEQ ID NO:2) used in cloning the phytoene synthase gene, crtB from *Erwinia uredovora* ATCC 19321 (synonym *Pantoea ananatis*). CrtB.F1 is a 59 mer sequence, carrying nucleotides (capital letters) specific to nucleotides 5797-5828 in the crt operon of *Erwinia herbicola* (synonym *Pantoea agglomerans*) Eho13 (GenBank accession no. M90698) and nucleotides (small letters) for the recognition sites (underlined) of restriction enzymes, which were used to ligate the crtB gene to a vector backbone or to a chloroplast transit peptide.

FIG. 2B depicts CrtB.R1 reverse primer sequence (SEQ ID NO:3) used in cloning the phytoene synthase gene, crtB from *Erwinia uredovora* ATCC 19321. CrtB.R1 is a 60 mer sequence, carrying nucleotides (capital letters) complementary to nucleotides 6655-6687 in the crt operon of *Erwinia herbicola* Eho13 (GenBank accession no. M90698) and nucleotides (small letters) for the recognition sites (underlined) of restriction enzymes, which were used to ligate the crtB gene to a vector backbone or to a transcription termination sequence.

FIG. 3A depicts Tps.F1 forward primer sequence (SEQ ID NO:5) used in synthesis of the transit peptide sequence, tps, a sequence encoding pea (*Pisum sativum*) chloroplast transit peptide and a leader sequence. Tps.F1 is a 61 mer sequence, carrying nucleotides (capital letters) specific to nucleotides 1144-1204 in pea gene for ribulose-1,5-bisphosphate carboxylase small subunit (rbcS) (GenBank accession no. X00806).

FIG. 3B depicts Tps.R1 reverse primer sequence (SEQ ID NO:6) used in synthesis of the tps sequence. Tps.R1 is a 64 mer sequence, carrying nucleotides (capital letters) complementary to nucleotides 1080-1243 in pea rbcS gene (GenBank accession no. X00806).

FIG. 3C depicts Tps.F2 forward primer sequence (SEQ ID NO:7) used in synthesis of the tps sequence. Tps.F2 is a 63 mer sequence, carrying nucleotides (capital letters) specific to nucleotides 1098-1160 in pea rbcS gene (GenBank accession no. X00806).

FIG. 3D depicts Tps.R2 reverse primer sequence (SEQ ID NO:8) used in synthesis of the tps sequence. Tps.R2 is a 51 mer sequence, carrying nucleotides (capital letters) complementary to nucleotides 1225-1256 in pea rbcS gene (GenBank acccession no. X00806) and nucleotides (italics) complementary to the sequence encoding the beginning of the leader sequence described in Shewmaker et al., Plant J., 20, 401-412, 1999.

FIG. 3E depicts Tps.F3 forward primer sequence (SEQ ID NO:9) used in synthesis of the tps sequence. Tps.F3 is a 53 mer sequence, carrying nucleotides (capital letters) specific to nucleotides 1086-1123 in pea rbcS gene (GenBank accession no. X00806) and nucleotides (small letters) for the recognition sites (underlined) of restriction enzymes, which were used to ligate the tps fragment to a vector backbone or to a promoter sequence.

FIG. 3F depicts Tps.R3 reverse primer sequence (SEQ ID NO:10) used in synthesis of the tps sequence. Tps.R3 is a 55 mer sequence, carrying nucleotides (italics) complementary to the sequence encoding the end of the leader sequence described in Shewmaker et al., Plant J., 20, 401-412, 1999, and nucleotides (small letters) for the recognition sites (underlined) of restriction enzymes, which were used to ligate the tps fragment to a vector backbone and to the crtB gene.

Abbreviations: Nt—non-transgenic tobacco, N2 and N5—two lines of transgenic tobacco. Heat Shock—lanes show expression of crtB gene in sprouts grown under heat shock. No H.S.—lanes show expression of crtB in sprouts grown in normal (ambient temperature) conditions. 0, 0.2, 1.0, 5 and 25 pg—quantities of synthetic crtB mRNA were loaded in the gel with 1 μg of non-transgenic carrier RNA.

Figures 8A, 8B:
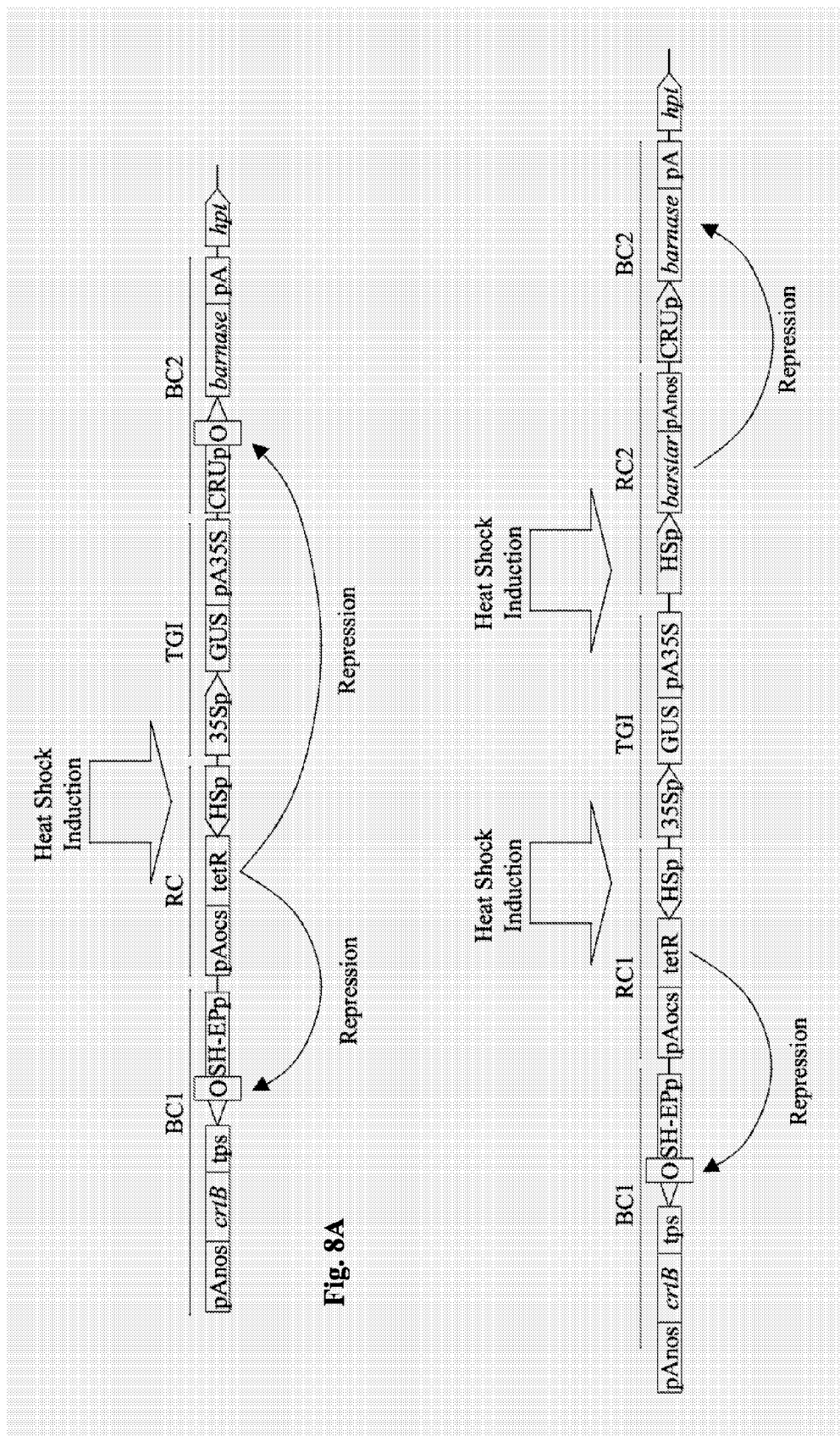

FIG. 8A depicts a RBF-system containing one recovering construct (RC). The construct contains GUS gene as TGI, tetR gene under HSp as RC, crtB gene under SH-EPp as BC1 and barnase under CRUp as BC2. Promoters of the BCs contain tet operator sequences (O). pAocs in the RC construct is octopine synthase polyA region.

FIG. 8B depicts a RBF-system containing two RCs. The construct contains GUS gene as TGI, tetR gene under HSp as RC1, barstar gene under HSp as RC2, crtB gene under SH-EP promoter containing tet operator sequences (O) as BC1 and barnase gene under CRU promoter as BC2.

Figure 9:
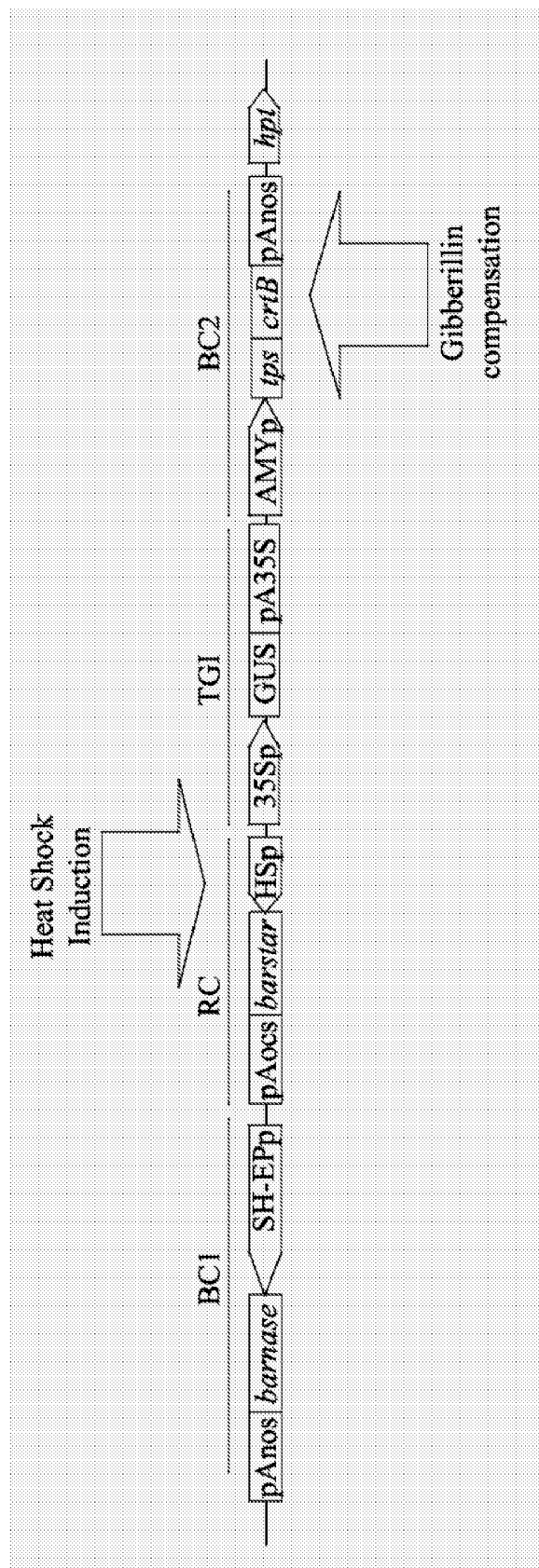

FIG. 9 depicts a DNA construct consisting of a double RBF-system, in which one BC1 (barnase) is recovered by induction of an RC (barstar) and another BC2 (crtB) is recovered by gibberellin and sucrose treatment. The BC1 consists of a barnase gene expressed under a SH-EPp and is recovered by an RC consisting of barstar gene driven by a HSp. The BC2 contains a crtB gene under an amylase promoter (AMYp) expressing specifically during the germination. The TGI is represented by a GUS gene.

Figure 10:
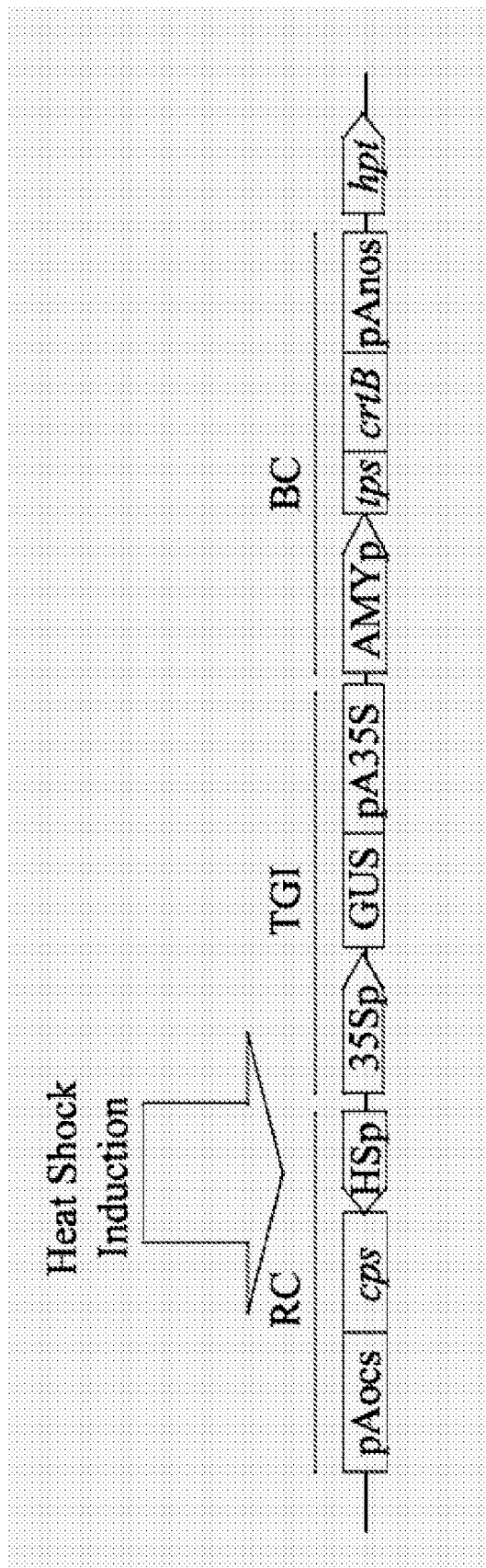

FIG. 10 depicts a DNA construct consisting of a RBF-system, in which the BC (crtB) is recovered by heat shock induction of an RC consisting of ent-copalyl diphosphate synthase gene (cps). The BC contains a crtB gene expressing under an AMYp. The TGI is represented by a GUS gene.

Figure 11:
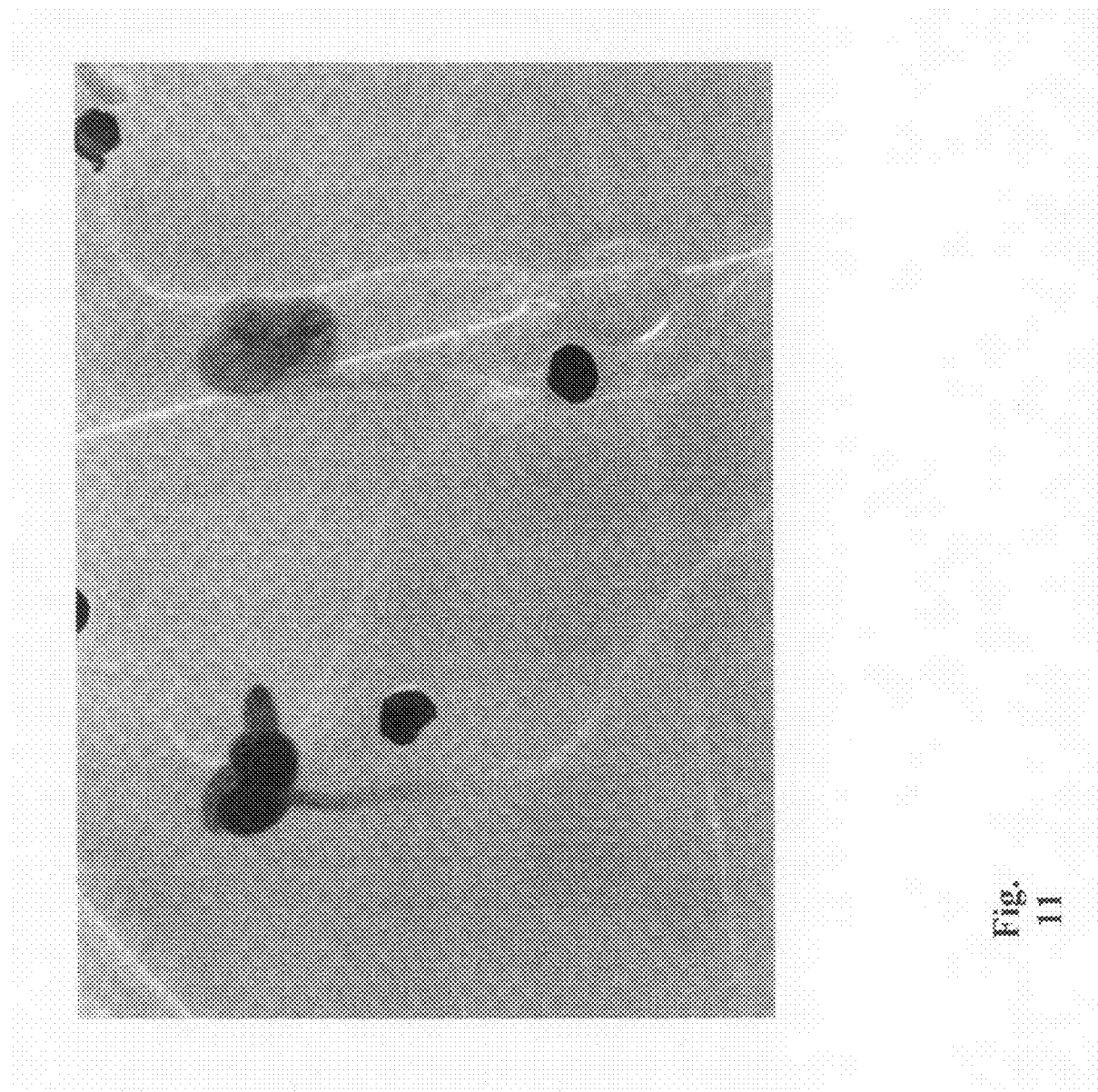

FIG. 11 depicts the effect of overexpression of a crtB gene on *Brassica* seedlings. The 5 transgenic seedling has a yellow/orange color due to overproduction of carotenoids and is incapable of forming the first true leaves. On the left side and the right side of FIG. 11, respectively, a non-transgenic control sprout and a transgenic sprout are shown.

Figure 12:
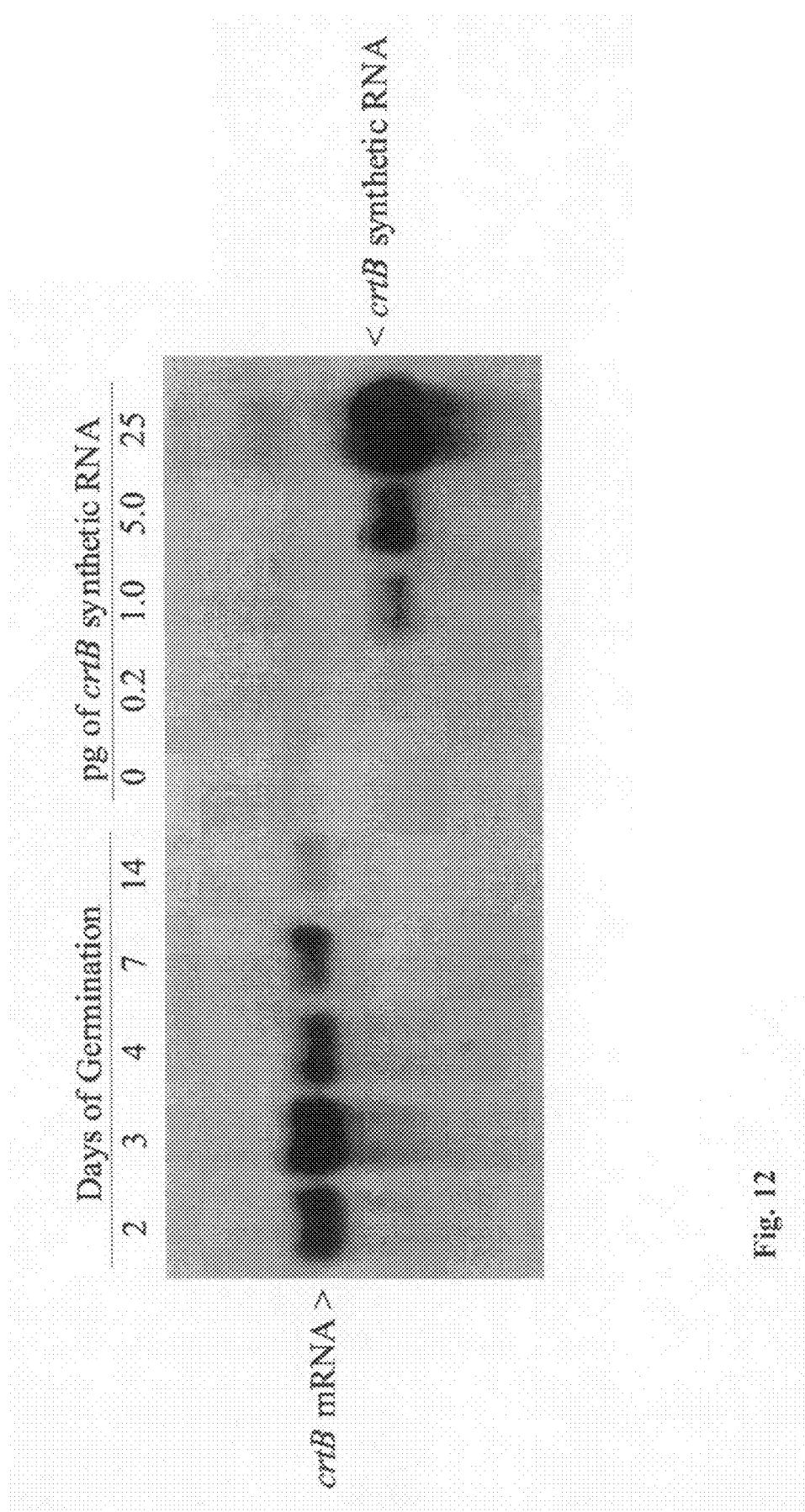

FIG. 12 depicts the expression of a crtB gene in sprouts of *B. napus*. 1 μg of total *B. napus* 10 sprout RNA was loaded in each lane. Synthetic control RNA was mixed with 1 μg of non-transgenic carrier RNA. The synthetic RNA of the crtB gene was shorter than mRNA because of the absence of a polyA tail. The expression of the crtB gene achieved a peek of expression (7 pg in 1 μg of total RNA) on the third day of the germination and faded to 0.3 pg after two weeks.

Figure 13:
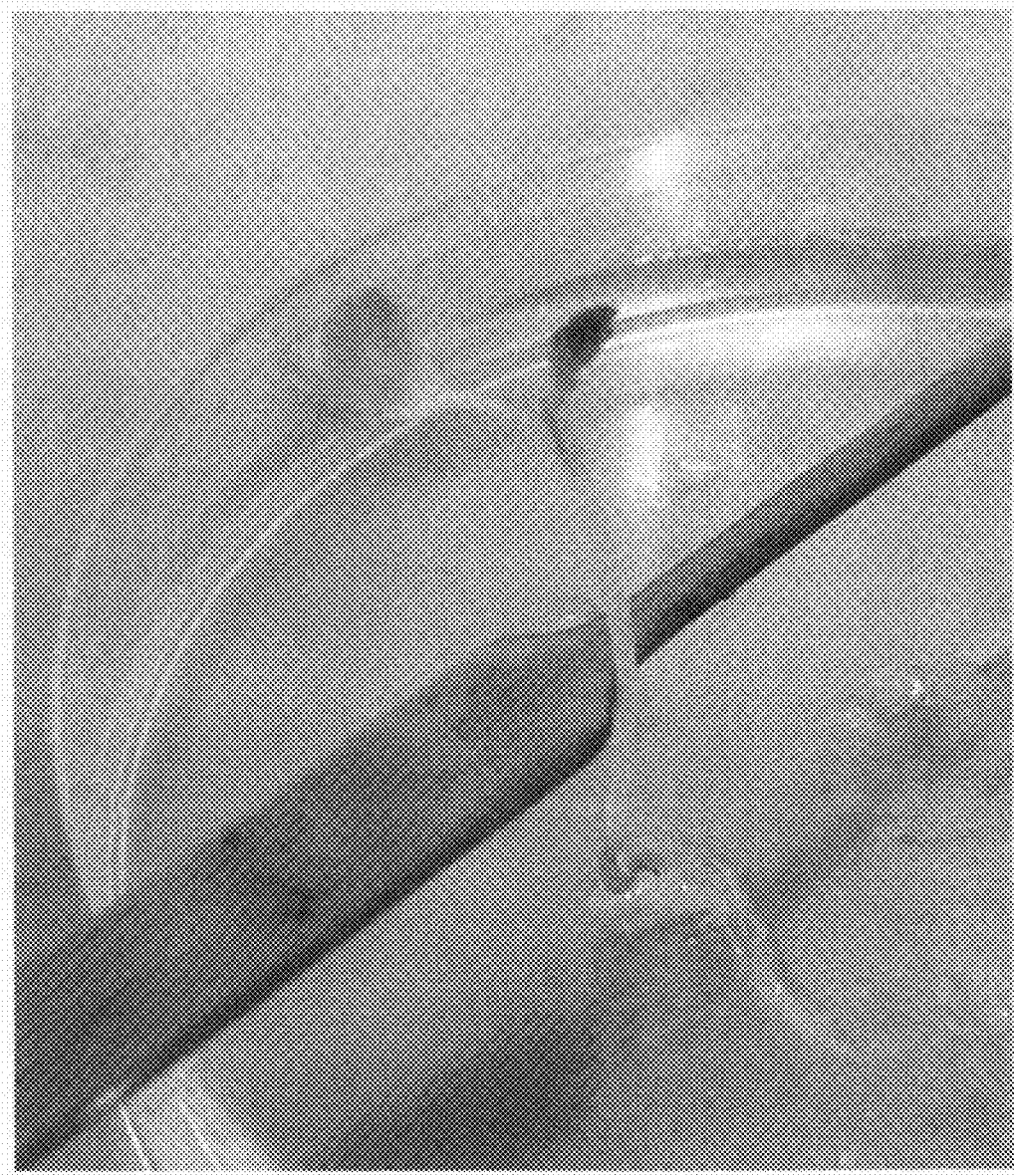

FIG. 13 shows a transgenic *Brassica* sprout carrying as a BC a crtB containing RBF-system, which grows on a medium containing gibberellin (10 mg/l GA$_3$) and sucrose (2%). Addition of gibberellin and sucrose has overcome the block caused by crtB expression. Therefore, the first emerging leaves are green.

DETAILED DESCRIPTION OF THE INVENTION

Terms used in the Disclosure

In the present disclosure most of the terms used have the same meaning as they generally have in the field of recombinant DNA techniques, molecular biology and in plant production related sciences. Some terms are however, used in a somewhat different way and are explained in more details below.

In this disclosure gene means an isolated and purified nucleotide sequence.

The term blocking construct means an expression cassette, a plasmid or vector construct, which comprises a blocking gene.

The term recovering construct means an expression cassette, a plasmid or vector construct, which comprises a recovering gene, which represses the blocked function.

The term recoverable block of function (RBF) system means a combination of BCs and RCs, which may be introduced into the plant cell or tissue as one or several inserts.

Simple Recoverable Block of Function System is a system without an RC construct. The recovery of blocked functions is obtained solely by an external intervention. A simple RBF-system is described in Example 1 and shown in FIG. 4.

One-insert system is synonymous to Single-insert system. Both of these terms mean that all components of the RBF-system are situated in the same DNA-insert and are integrated into one site of the plant genome/chromosome. One-insert systems are described in Examples 1-5.

Two-insert system means that the blocking construct(s) (BCs), comprising at least one crtB gene and the recovering construct(s) (RCs) with promoters and markers are placed in separate DNA inserts, vectors or plasmids and these BC and RC constructs are subsequently inserted one by one. The two-insert system is exemplified in a so called Segregating Recoverable Block of Function System which is synonymous to Delayed Recoverable Block of Function system. Both of these terms describe a RBF-system in which the RC(s) is situated in a different DNA insert than the BC(s). After plant transformation the RC(s) is integrated into a different non-allelic chromosome apart from the BC(s) and the TGI.

Detailed Description Of The Invention

The present inventors have demonstrated that germination-specific overexpression of phytoene synthase in contrast to constitutive, seed specific and embryo-specific expression not only delays, but prevents germination of transgenic seeds carrying the crtB gene. Furthermore, the present inventors demonstrated that the blocked germination could be recovered by a user controlled intervention including the treatment of germinating seeds with gibberellin and sugar or through induction of an RC.

Based on preliminary observations, which indicated that the nucleotide sequences encoding phytoene synthase could be useful as blocking genes for controlling transgene segregation, the inventors designed a plant transformation vector or BC comprising a crtB gene (SEQ ID NO:1) from *Erwinia uredovora* expressing under Heat Shock promoter of *Glycine max* (GenBank accession number M28070; Czarnecka et al., Mol. Cell. Biol., 9, 3457-3463, 1989). In one embodiment of the invention, targeted expression in chloroplasts or plastids was achieved with a BC, which included a transit peptide sequence (tps) (SEQ ID NO:4) of pea (*Pisum sativum*) ribulose-1,5-bisphosphate carboxylase small subunit gene (rbcS) (GenBank accession no. X00806) and a leader sequence (Shewmaker et al., Plant J., 20, 401-412, 1999). The crtB gene acted as a blocking gene in the germinating seeds and the overexpression of phytoene synthase depleted the synthesis of a precursor for chlorophyll together with overproduction of carotenoids. This led to phenomena, which herein is called "golden sprouts". The depletion of the gibberellin precursor led to a blocked germination, because gibberellin is an essential hormone, which regulates the germination process. Because the transgenic seeds could not germinate in natural conditions, no reproducing plants were formed either.

It was demonstrated that the expression of crtB gene in germinating seeds in moderate or high levels (mRNA>1 pg/μg of total RNA) resulted in total blocking of the germination. It was possible to recover the blocked germination caused by deficiency of gibberellin and sugars in the germinating seed by an external addition of an effective amount of gibberellins or gibberellic acid and carbohydrates (sugars) or by repression of the promoter expressing the crtB gene. The advantage of the crtB gene is that occasional overexpression of the phytoene is not crucially adverse in the other stages of plant development.

Examples of suitable germination specific promoters are the promoter of sulfhydryl (cysteine) endopeptidase (SH-EP) of *Vigna mungo* (GenBank accession number X51900; Yamauchi et al., Plant Mol. Biol., 30, 321-329, 1996), amylase promoter (Mita et al. Plant Physiol, 1995, 107: 895-904, Gene bank as. No. s77076) and the Heat Shock promoter (HSp) from *Glycine max* (GenBank accession number M28070; Czamecka et al., Mol. Cell. Biol., 9, 3457-3463, 1989) or *Vicia faba*. The Heat Shock promoter is induced by a heat shock treatment and has a strong germination specificity in *Brassica napus*, but a weak germination specificity in tobacco.

Accordingly, the present disclosure is related to nucleotide sequences encoding phytoene synthase, which when allowed to express under the control of germination specific promoters or a promoter constitutively repressed by an RC, are useful in any methods for controlling transgene segregation or transgene containment and for designing RBF-systems, for methods or systems which require a nucleotide sequence, which blocks an essential function, which block may be recovered by a user controlled interventions with or without a suitable RC.

The means for recovering the blocked germination is a user controlled treatment in which the seeds are contacted with an effective amount of gibberrellin or gibberellic acid and/or sugar, preferably sucrose. The effective amount is an amount that blocks the germination of the transgenic seed. The effective amount for gibberellin or gibberellic acid is at least 2 mg/l, preferably 5-10 mg/l . The effective amount of carbohydrate or sugar, when it is represented by sucrose at least 2%, preferably at least 3% sugar.

Figure 1:
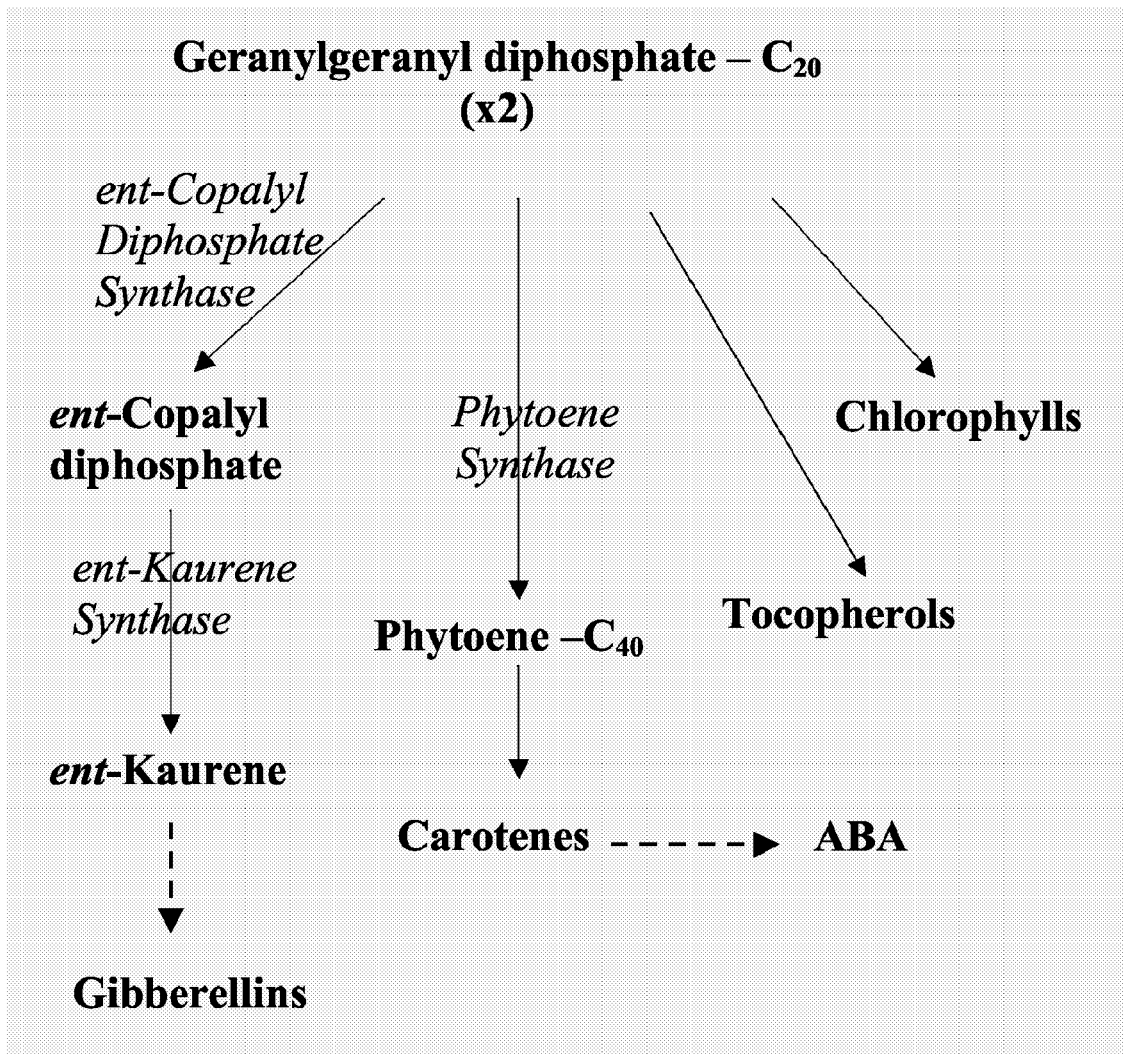
FIG. 1 depicts a scheme of biosynthetic pathways starting from the key molecule—geranylgeranyl diphosphate. Two geranylgeranyl diphosphate (C20) moieties are condensated to form a carotenoid precursor, phytoene (C40). The enzyme responsible for this reaction is phytoene synthase encoded by crtB gene. Geranylgeranyl diphosphate is also a precursor in synthesis of carotenes, gibberellins, chlorophylls and tocopherols.

In the RBF-system, the RC may comprise a nucleotide sequence, which encodes an enzyme involved in the synthesis of metabolites, which due to the overexpression of phytoene synthase have been depleted in the plant. Such nucleotide sequences are the sequences encoding the enzymes ent-copalyl diphosphate synthase or ent-kaurene synthase, which are important in the synthesis of certain metabolites in the gibberellin biosynthetic pathway shown in FIG. 1. Genes encoding ent-copalyl diphosphate synthase and ent-kaurene synthase may be isolated from several plant species, for example from *Arabidopsis* (Fleet et al., Plant Physiol., 132, 830-839, 2003). Such genes have also been cloned from rice (*Oryza sativa*) (AY602991; Prisic et al., Plant Physiol., 136, 4228-4236, 2004; GenBank accession number AY347882; Margis-Pinheiro et al., Plant Cell Rep., 23, 819-833, 2005), from barley (*Hordeum vulgare*) (GenBank accession number AY551436; Spielmeyer et al., Theor. Appl. Genet., 109, 847-855, 2004) and tobacco (*Nicotiana tabacum*) (GenBank accession number AB170035; Ishida et al., Plant Cell 16, 2641-2651, 2004).

The applicability of the crtB gene is disclosed in the following examples.

EXAMPLE 1

Simple RBF-system containing one BC without RCs *Brassica napus* plants expressing crtB gene produce seeds, which germinate only after adding gibberellic acid and sucrose.

a. Cloning of the Gene Encoding Phytoene Synthase, crtB (SEQ ID NO:1) from *Erwinia uredovora* (synonym *Pantoea ananatis*)

The gene encoding phytoene synthase, crtB (SEQ ID NO:1) was cloned by high fidelity PCR from *Erwinia uredovora* (*Pantoea ananatis*) ATCC19321. Genomic DNA was isolated as described herein.

An aliquot of an overnight culture of *E. uredovora* ATCC 19321 in Luria-Bertani (LB) broth was suspended in 90 µl of 50 mM Tris-HCl (pH 8.0)—5 mM EDTA, supplemented with 500 µg of RNAseA. 10 µl of 10SDS was added and the viscose suspension was placed at 60° C. for 5 minutes. 500 µl of the 4 M ammonium thiocyanate—100 mM Tris-HCl (pH 8.0)—25% EtOH (ATC-solution) was added to the lysed bacterial extract, and the mixture was transferred to a hand-made column of glass microfibre GF/C (Whatman). The column was centrifuged at 5000 rpm for 1 min, and the bound material was washed with additional 1 ml of ATC-solution, and further with 1 ml of 4.2 M guanidine-HCl—40% isopropanol. Column was washed three times with 75% ethanol and DNA was eluted in 100 µl of distilled water. Concentration of the purified DNA was approximately 30 ng/µl.

Primers for crtB gene synthesis were designed according to the crtB sequence of *E. herbicola* (synonym *Pantoea agglomerans*) Eho13 carotenoid biosynthesis gene cluster (GenBank accession number M90698; To et al., Microbiol., 140, 331-339, 1994). Primers carried recognition signals for the restriction enzymes, which were used in ligating the crtB gene into vector backbones and to the tps transit peptide sequence. The CrtB.F1 (SEQ ID NO:2) and CrtB.R1 (SEQ ID NO:3) primer sequences are presented in FIG. 2.

Dynazyme DNA polymerase II (Finnzymes) mediated PCR amplification of crtB was carried out in a thermal cycler with a heated lid (PTC-200 Peltier Thermal Cycler, MJ Research). Reaction mixture (25 µl) contained 200 µM dNTP-mixture, 0.6 µM CrtB.F1 primer, 0.6 M CrtB.R1 primer, 100 ng *E. uredovora* ATCC 19321 DNA, 1x Dynazyme DNA polymerase buffer, 0.6 U Dynazyme DNA polymerase II. Initial denaturation was carried out at 94° C. for 2 minutes, followed by 30 cycles of: denaturation at 94° C. for 40 seconds, annealing at 55° C. for 40 seconds, and extension at 72° C. for 2 minutes. Final extension was carried out at 72° C. for 8 minutes. The PCR amplification yielded a DNA fragment of approximately 900 bp (SEQ ID NO:1).

b. Cloning of the Pea Transit Peptide Sequence, tps (SEQ ID NO:4) from *Pisum sativum*

In order to target the phytoene synthase gene into chloroplasts or plastids, a transit peptide sequence, tps (SEQ ID NO:4) was synthetized. The DNA fragment encodes the transit peptide of a pea (*Pisum sativum*) Rbc Small Subunit (GenBank accession number X00806; Coruzzi et al., EMBO J., 3, 1671-1679, 1984; Misawa et al., Plant J., 4, 833-840, 1993), preceded by a leader sequence (Shewmaker et al., Plant J., 20, 401-412, 1999). The tps sequence was synthetized chemically by PCR in three steps by using the Pfu DNA polymerase (Promega). In the first reaction a DNA fragment containing nucleotides 1144-1243 in the X00806 sequence was synthetized from two partially complementary oligonucleotide primers, Tps.F1 (SEQ ID NO:5) and Tps.R1 (SEQ ID NO:6). In the second reaction by using the first reaction mix as a template and two new oligonucleotide primers, Tps.F2 (SEQ ID NO:7) and Tps.R2 (SEQ ID NO:8), a DNA fragment containing nucleotides 1098-1256 in the X00806 sequence and the beginning of the leader sequence was synthetized. In the third reaction by using the second reaction mix as a template and two new oligonucleotide primers, Tps.F3 (SEQ ID NO:9) and Tps.R3 (SEQ ID NO:10), a DNA fragment containing nucleotides 1086-1256 in the X00806 sequence and the rest of the leader sequence was synthetized. Oligonucleotide primers used in the third reaction carry recognition signals for the restriction enzymes, enabling vector cloning and ligation to the crtB sequence. The primer sequences Tps.F1 (SEQ ID NO:5), Tps.R1 (SEQ ID NO:6), Tps.F2 (SEQ ID NO:7), Tps.R2 (SEQ ID NO:8), Tps.F3 (SEQ ID NO:9) and Tps.R3 (SEQ ID NO:10) are presented in FIG. 3.

The first PCR amplification reaction was carried out in a thermal cycler with a heated lid (PTC-200 Peltier Thermal Cycler, MJ Research). Reaction mixture (25 µl) contained 50 µM dNTP-mixture, 0.6 µM Tps.F1 primer, 0.6 µM Tps.R1 primer, 1x Pfu DNA polymerase buffer, 0.9 U Pfu DNA polymerase (Promega). Initial denaturation was carried out at 94° C. for 45 seconds, followed by 5 cycles of: denaturation at 94° C. for 40 seconds, annealing at 70° C. for 40 seconds, and extension at 72° C. for 1 minute. Final extension was carried out at 72° C. for 2 minutes.

The second PCR amplification was similar to the first PCR, except that 2.5 µl of the first reaction mixture was used as a template and the reaction consisted of 20 cycles of denaturation, annealing and extension. Third PCR amplification used 2.5 µl of the second reaction as a template and 15 cycles of denaturation, annealing and extension. The PCR amplification yielded a DNA fragment of approximately 243 bp (SEQ ID NO:4).

c. Designing an Expression Cassette or BC for a Simple RBF-System

A tps-crtB construct, which expressed under the inducible Heat Shock promoter (HSp) from Soy Bean (*Glycine max*) (GenBank accession number M28070; Czarnecka et al., Mol. Cell. Biol., 9, 3457-3463, 1989) was designed. To ensure termination of transcription, the polyA region from the *Agrobacterium tumefaciens* nopaline synthase (nos) gene (GenBank accession number V00087; Depicker et al., J. Mol. Appl. Genet., 1, 561-573, 1982; Bevan et al., Nucl. Acid.

Res., 11, 369-385, 1983) was included. Said expression cassette was introduced into a pCAMBIA1301 (Cambia) binary vector for plant transformations by replacing the 2.8 kb BamHI-NheI fragment of pCAMBIA1301 with the crtB expression cassette, which consisted of the *Glycine max* Heat Shock promoter (HSp), the synthetic tps sequence (SEQ ID NO:4) encoding pea RbcS chloroplast transit peptide, the synthetic *E. uredovora* phytoene synthase (crtB) gene (SEQ ID NO:1), and the *A. tumefaciens* nopaline synthase polyA region. The vector contained a hygromycin resistance marker as a representative of transgene of interest (TGI), driven by the constitutive 35S promoter (35Sp) of Cauliflower mosaic virus (CaMV) and terminated by CaMV35S polyA. The components of said simple RBF-system are presented in FIG. 4. The kanamycin resistance marker in pCAMBIA backbone was used for bacterial selection and the hygromycin resistance marker (TGI) was used for plant cell/tissue selection.

d. Plant Transformation (Electroporation and *Agrobacterium* Mediated Transformation)

The simple RBF-system consisting of a HSp-tps-crtB-pA-nos as a BC construct and a 35Sp-hpt-pA as a TGI construct (FIG. 4) was transformed into electrocompetent *A. tumefaciens* strains C58C1, carrying the pGV3850 helper plasmid (Zambryski et al., EMBO J., 2, 2143-2150, 1983) and LBA4404, carrying the pAL4404 helper plasmid (Hoekema et al., Nature, 303, 179-180, 1983) by using a Bio-Rad electroporation apparatus, and maintained on YEB medium supplemented with 50 mg/l kanamycin and 50 mg/l rifampicin. YEB medium consisted of 2.5 g/l yeast extract—5 g/l peptone—2.5 g/l triptone—0.5 g/l $MgSO_4 \times 7\ H_2O$—5 g/l sucrose—15 g/l agar.

Hypocotyls of *B. napus* and leaf segments of *N. tabacum* were transformed by *A. tumefaciens* LBA4404 inoculation. Regenerated shoots were selected on hygromycin and checked for transgene integration using PCR. PCR-positive shoots were grown in the greenhouse and were self-pollinated. When expressing under a heat shock inducible promoter in tobacco plants, HSp exhibited germination (first 3 to 7 days) specificity in oil seed and tobacco plants. Transgenic plants overexpressing crtB gene were dwarfish and had yellowish inclusions on leaves. The normal phenotype plants were selected to produce seeds e. Demonstrating the Blocking Effect of crtB Expression in Tobacco Plants and *B. napus*.

Figure 4:
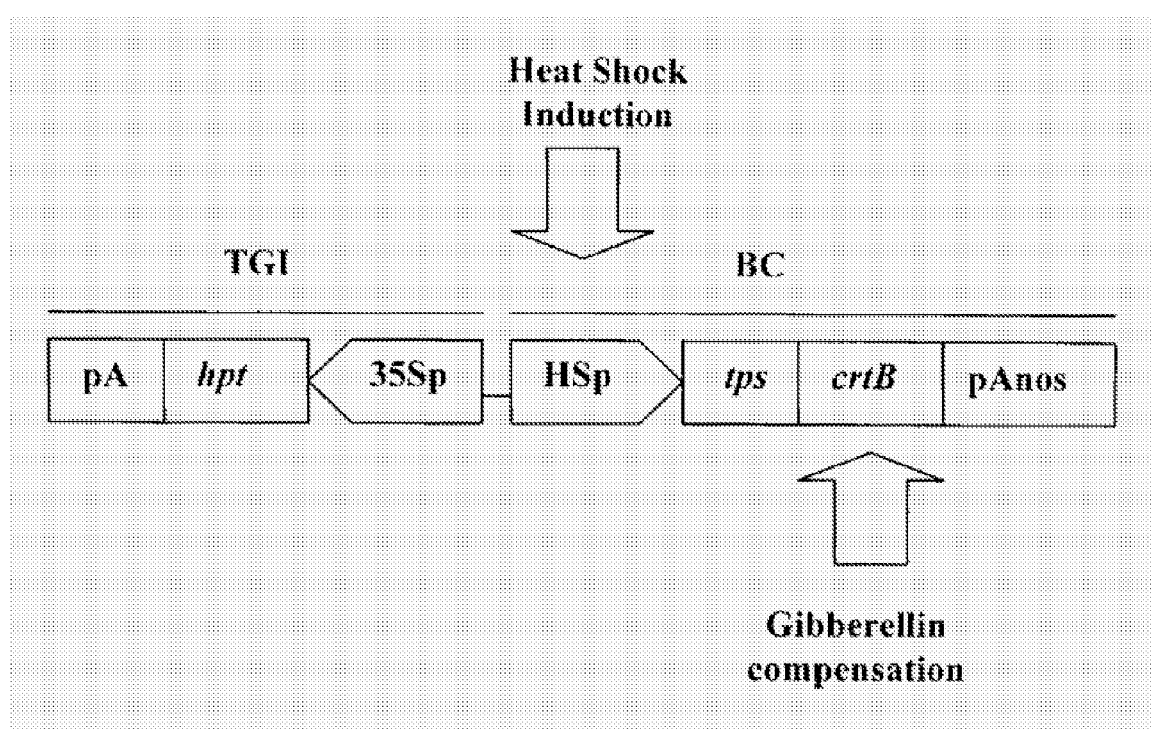
FIG. 4 depicts a simple RBF-system containing one blocking construct (BC) and a selection marker (hpt gene) as a representative of transgene of interest (TGI). BC consists of the phytoene synthase gene (crtB gene) from *Erwinia uredovora* (*Panthoea ananatis*) ATCC 19321 headed by tps, the pea rbcS chloroplast transit peptide sequence with a leader sequence. The crtB gene expression is driven by a Heat Shock promoter (HSp) from Glycine max and terminated by a nopalin synthase polyadenylation signal from *Agrobacterium tumefaciens* (pAnos). The hpt gene encoding hygromycin phosphatase is driven by a 35S promoter (35Sp) from Cauliflower mosaic virus (CaMV).

In vitro grown tobacco leaf segments were transformed with *Agrobacterium tumefaciens* carrying a transgenic construct, which is described in Example 1 (c) above and shown in FIG. 4. Recovered transgenic shoots were applied to heat shock at +42° C. for two hours. Transgenic tobaccos expressing crtB gene after heat shock were chosen for experiments.

Figure 5:
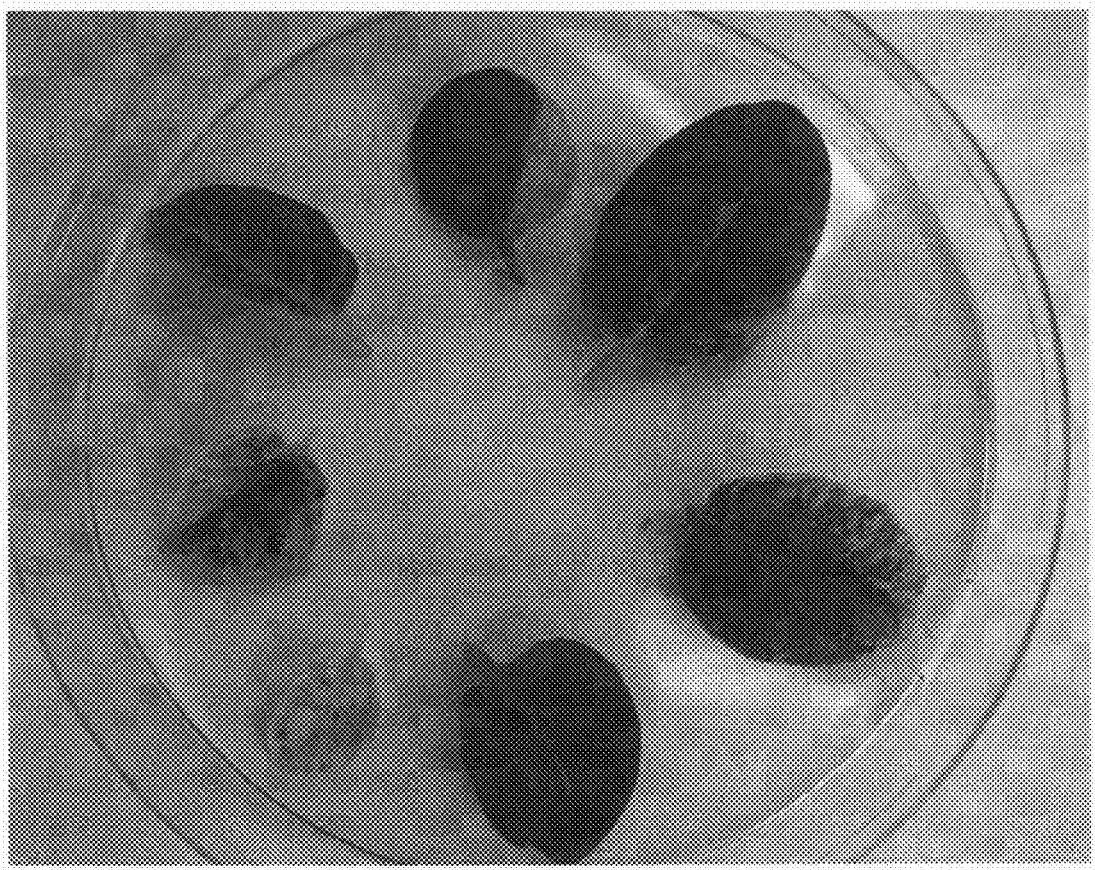
FIG. 5 depicts expression of crtB gene in leaves of in vitro tobacco (*Nicotiana tabacum*) plants. Due to high expression of phytoene synthase, the yellow color of carotenoids substituted the green color of chlorophyll.
Figure 6A:
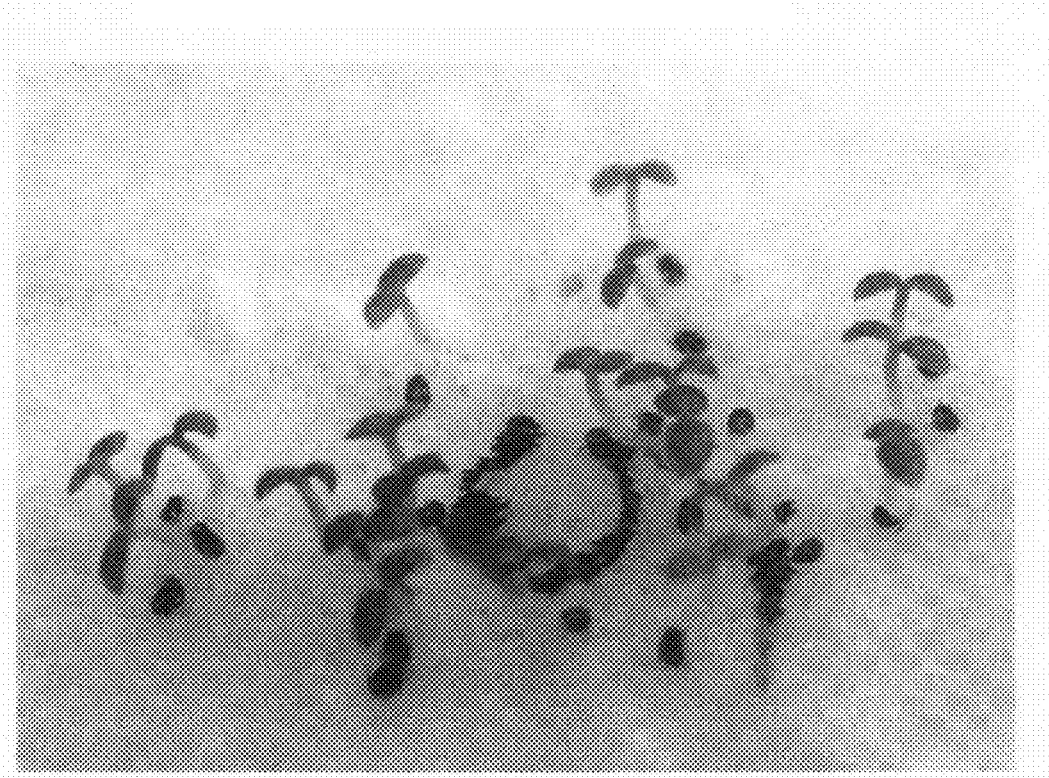
FIG. 6A depicts tobacco sprouts carrying the HSp-tps-crtB construct. Sprouts germinating in room temperature are green-colored or slightly yellowish.
Figure 6B:
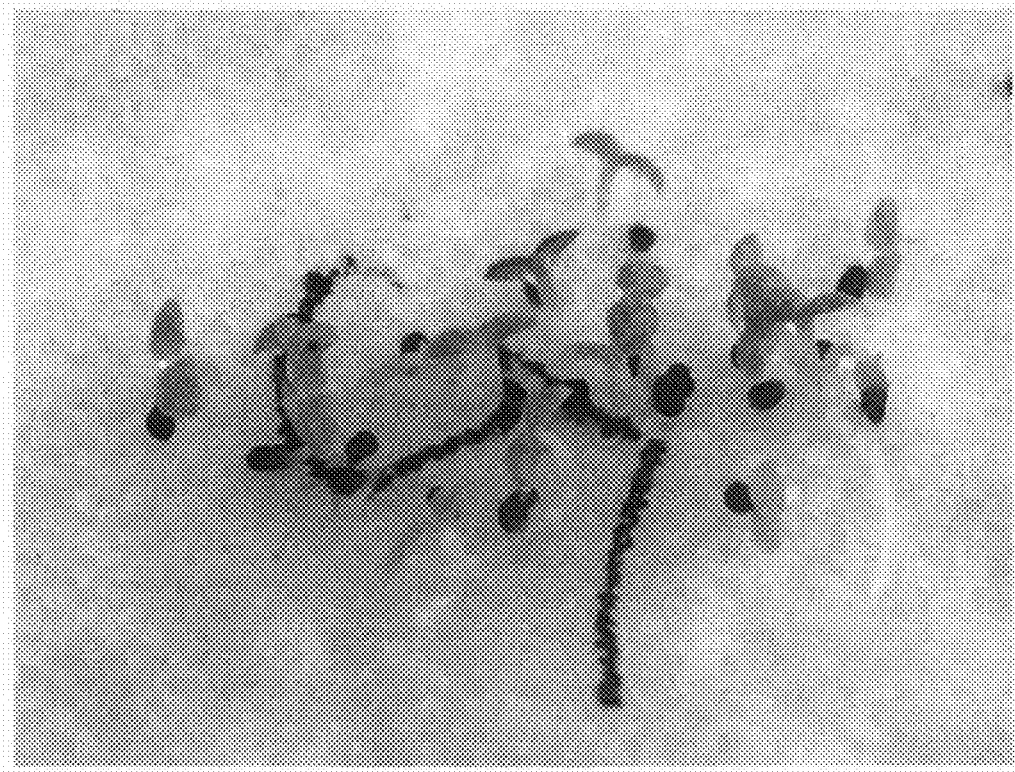
FIG. 6B depicts effect of heat shock treatment on the tobacco sprouts carrying the HSp-tps-crtB construct. Sprouts from the same transgenic line as in FIG. 6A became yellow after heat shock treatment (1 hour at 42° C. every day). The yellow-colored sprouts could not produce the first true leaves, remaining to the stage of cotyledon expansion. Green sprouts occurred approximately in ratio 1:15.
Figure 7:
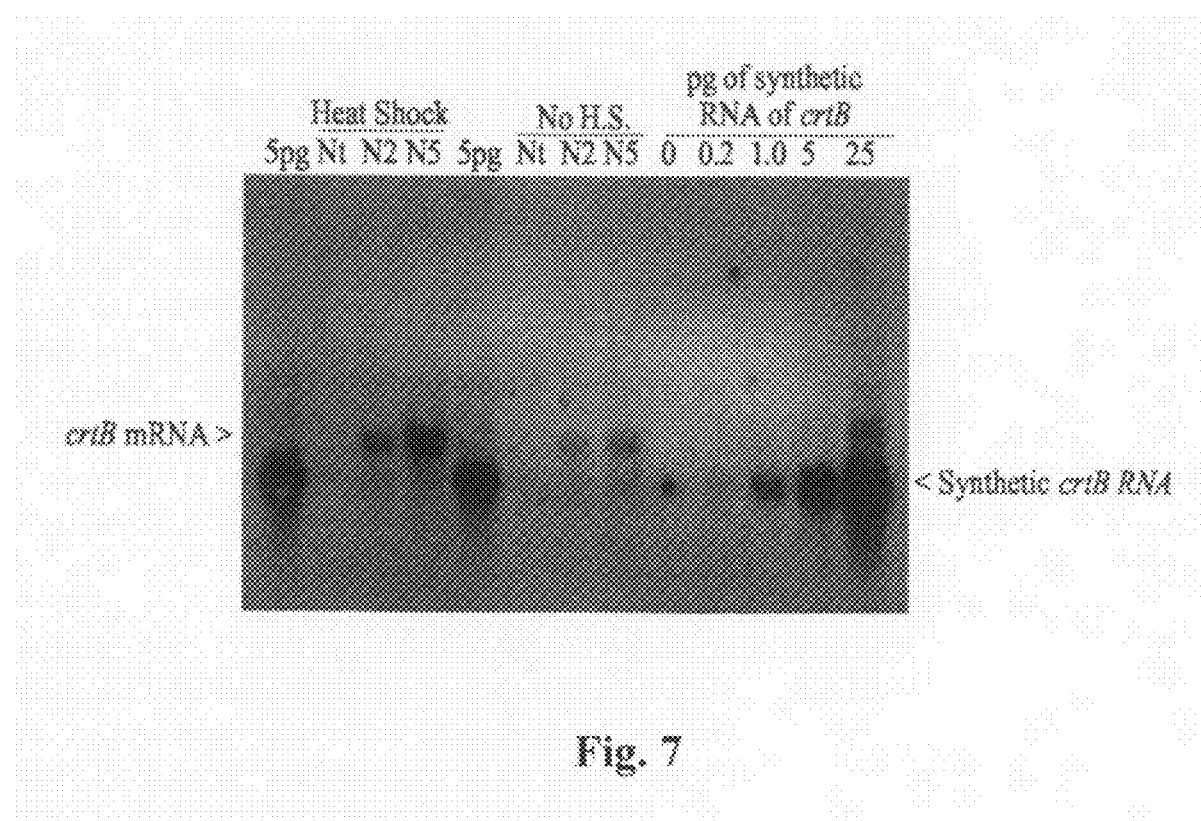
FIG. 7 depicts Northern analysis of crtB expression in sprouts germinated under heat shock and in normal conditions. 1 μg of total RNA from *N. tabacum* sprout was loaded in each lane. The synthetic RNA of crtB gene was shorter than the mRNA due to the absence of polyA tail. The mRNA levels of transgenic sprouts expressing crtB gene were 0.3-0.6 pg in normal conditions and 0.7-3.0 pg after heat shock treatment per 1 μg of total RNA.

During heat shock treatment the expression of the crtB gene varied from strongly constitutive to specific. The different levels of expressions were demonstrated as color variations in the leaves. The colors varied from green to yellow spotted leaves to totally yellow leaves as shown in FIG. 5. Plants having a normal phenotype or being slightly yellow-colored were grown in greenhouse and were used to produce transgenic seeds, which were allowed to germinate on wet paper in room temperature and in heat shock conditions for one hour at 42° C. each day. Transgenic sprouts in heat shock conditions were yellow and could not produce the first true leaves, while control sprouts were green and grew normally like non-transgenic plants (FIG. 6). Green sprouts appeared among yellow ones in a frequency of 1:15, which probably indicated that two independent transgenic inserts had been introduced in the genome. Northern analysis demonstrated that the block of germination was caused by expression of crtB gene at a level of 3 pg mRNA per μg of total RNA as shown in FIG. 7. After heat shock treatment a block of germination was demonstrated in 70% of the sprouts of one of the lines used, whereas sprouts of the same line demonstrated in average a one week delay in germination. The germination of sprouts on 3% sugar media was slightly inhibited in both transgenic lines and control lines. Gibberellic acid ($GA_3$) in a concentration of 1-3 mg/l promoted germination of sprouts treated with heat shock.

Transgenic *Brassica* seeds expressing crtB gene developed yellow-orange colored sprouts ('golden sprouts') as shown in FIG. 11. In natural conditions the orange sprouts can not grow further after the stage of expanding cotyledons. When expressing during early germination stage under HS promoter, the crtB gene overproduced phytoene synthase and depleted the mutual source for synthesis of those molecules. Lack of precursor for chlorophyll together with overproduction of carotenoids led to phenomena of 'golden sprouts'. Lack of gibberellin precursor led to block of germination, because the gibberellin is the essential hormone regulating germination process. crtB gene acted as a BC in the germinating seeds by decreasing the content of gibberellin. Therefore, the transgenic plants could not grow and reproduce in natural conditions.

Expression of crtB gene was demonstrated in Northern analysis from seedlings of *B. napus* of different ages. (FIG. 13). The transgenic seeds were sterilized in 2% Na hypochlorite and germinated aseptically on MS (Murashige-Skoog) agar. The "golden sprouts" were collected on the 2nd, 3rd, 4th, 7th and 14th day of germination. Total RNA was isolated as described earlier. The samples were run in an agarose gel and hybridized with a Digoxinin labeled RNA probe prepared based on the crtB gene. The expression of the crtB mRNA was compared to a synthetic non-labeled RNA loaded in the same gel/blot in different amounts. The expression of phytoene synthase mRNA increased from 1 pg/μg of total RNA on day 2 to 4 pg/μg on day 4 of germination. crtB expression continued for one week and faded after about two weeks.

f. Recovery of the Blocked Function

The action of the RBF-system was demonstrated in germination tests and in order to recover the blocked germination function, external addition of gibberellins and sucrose were applied in different concentrations. Seeds were sterilized in Na-hypochlorite and thereafter they were allowed to germinate on Murashige Skoog (MS) agarose media. 'Golden sprouts' could not grow further than to the stage of cotyledon expansion on media lacking sucrose and gibberellic acid. Addition of 2% sucrose increased the growth rate and the size of the sprouts was doubled. The sprouts developed to full-size cotyledons, but could not produce the first leaves. Gibberellic acid in a concentration of 1-1.5 mg/l had no effect on the transgenic sprouts, but blocked germination of non-transgenic sprouts. Golden sprouts could germinate, but had to be transferred onto MS media without gibberellin on day 3-7 after the start of germination in order to continue germination.

On MS media supplemented with 2% sucrose and 10 mg/l GA$_3$ transgenic sprouts produced the first green leaves and thereby overcame the blocked germination (FIG. 13). Gibberellic acid alone, without sucrose addition was unable to recover the germination function. Therefore, recovery of the block of germination due to expression of crtB gene was enabled only by addition of sucrose and gibberellic acid in combination. Thus, the external intervention in this case was addition of sucrose and gibberellic acid. Optimal conditions for transgenic *B. napus* seedlings were 2% sucrose and 5-10 mg/l GA$_3$.

EXAMPLE 2

Double RBF-system, in which TGI (GUS) is between two BCs which contain different blocking sequences: phytoene synthase (BC1) and barnase (BC2). Promoters of BCs contain TetR repressor binding sequence (tetO—tet operator). The double RBF-system comprises one RC encoding TetR repressor protein.

A RBF-system is designed, wherein BCs flank the TGI and RC as shown in FIG. 8A. The BC1 consists of a crtB gene (SEQ ID NO:1) from *Erwinia uredovora*, which crtB gene driven by SH-EP promoter (SEQ ID NO:11) of *Vigna mungo* encodes a phytoene synthase. The BC2 is designed either from a barnase 1 synthetic coding sequence (SEQ ID NO:12) or a barnase 2 synthetic coding sequence (SEQ ID NO:13) driven by a CRU promoter (SEQ ID NO:14) of *Brassica napus*. The SH-EP and CRU promoters have a modified 3' end, wherein the vicinity of TATA boxes (SEQ ID NO:15) is modified as shown in SEQ ID NO:16 and SEQ ID NO:17, respectively, in order to contain three tet operators (SEQ ID NO:18) from an *Escherichia coli* transposon Tn10. The RC consists of a TetR gene (SEQ ID NO:19) driven by Heat Shock promoter of *Glycine max* or *Vigna mungo*.

The phytoene synthase (BC1), when expressed in embryos and germinating seeds, redirects metabolites from the gibberellin pathway to the synthesis of carotene precursor phytoene and consequently carotenoids and abscidic acid. The enhanced carotenoid synthesis leads to incapability of germinating seeds to grow and produce photosynthesizing plants. Morphologically the sprouts look yellow-orange in color and cannot grow further than to the stage of cotyledon expansion (as shown on FIG. 6). The Barnase (BC2) expressed under CRU promoter digests RNA molecules in the embryos, which leads to the symptom of dried flowers and incapability of seeds to develop. Both of the blocking genes are expressed in natural conditions if the RC is not activated.

Application of heat shock (1-2 hours at 42° C. every second day) during flowering and seed development enables maturation of seeds. Heat shock application during seed germination enables germination of seeds beyond the stage of cotyledon expansion. The heat shock application induces the expression of Tet repressor from the RC, which binds the tet operators in the promoters in the BCs, thereby making the BCs inactive.

EXAMPLE 3

Double RBF-system, in which TGI (GUS) is between two BCs which contain different blocking sequences: phytoene synthase (BC1) and barnase (BC2). Promoter of BC1 contains TetR repressor binding sequence (tetO—tet operator). The double RBF-system comprises two RCs. RC1 encodes TetR repressor protein driven by HS promoter and RC2 contains barstar gene under HS promoter.

A RBF-system which consists of BCs flanking the TGI and RCs as shown in FIG. 8B is designed. The BC1 consists of crtB gene (SEQ ID NO:1) from *Erwinia uredovora*. This crtB gene encodes phytoene synthase and is driven by a SH-EP promoter (SEQ ID NO:11) of *Vigna mungo*, which has a modified 3' end, wherein the vicinity of the TATA box (SEQ ID NO:15) is modified as shown in SEQ ID NO:16, to contain three tet operators (SEQ ID NO:18) from *Escherichia coli* transposon Tn10. BC2 consists of barnase 1 synthetic coding sequence (SEQ ID NO:12) or barnase 2 synthetic coding sequence (SEQ ID NO:13) driven by the CRU promoter (SEQ ID NO:14) of *Brassica napus*. The RC1 consists of tetR gene (SEQ ID NO:19) driven by Heat Shock promoter of *Glycine max* or *Vigna mungo*. The RC2 consists of plant adapted synthetic coding sequence of barstar gene (SEQ ID NO:20) driven by the Heat Shock promoter.

EXAMPLE 4

Double RBF-system, in which TGI (GUS) is between two BCs containing different blocking genes: barnase and phytoene synthase. The system contains one RC which encodes barstar gene under Heat Shock promoter. Recovery of phytoene synthase action is performed by gibberellin and sucrose treatment.

An RBF-system is designed with a BC containing a GUS gene as the TGI, a barnase gene (SEQ ID NO:12 or SEQ ID NO:13) expressing under the control of a SH-EP promoter in BC1, a crtB gene (SEQ ID NO:1) under amylase promoter (Mita et al. Plant Physiol, 1995, 107: 895-904, Gene bank as. No. s77076) in BC2, barstar gene (SEQ ID NO:20) under Heat Shock promoter in RC, and selection marker hpt gene. Positions of the genes are shown in the FIG. 9. Transgenic plants cannot produce germinating seeds in normal conditions. To reproduce normally the plants need heat shock treatment at 42° C. for 1-2 hours every second day during fruit maturation and gibberellin-sucrose support during germination.

EXAMPLE 5

RBF-system consisting phytoene synthase gene under SH-EP promoter as BC and ent-copalyl diphosphate synthase gene under HS promoter as RC A RBF-system is designed in which the BC contains a GUS gene as a TGI, a phytoene synthase (crtB) gene as the blocking gene, an ent-copalyl diphosphate synthase (cps) gene as an RC and an hpt gene as a selection marker. Positions of the genes are shown in the FIG. 10. CrtB gene is controlled by an Amylase promoter (AMYp) originating from *Arabidopsis thaliana* (Mita et al. Plant Physiol, 1995, 107: 895-904, Gene bank as. No. s77076) and cps gene by heat shock (HSp) promoter.

Overexpression of phytoene synthase during the germination results in lack of gibberellins and blocks the germination on the stage of expanding cotyledons. To germinate normally, the seedlings need heat shock treatment (42° C. for 1-2 hours every second day) during germination. Heat shock induces overexpression of ent-copalyl diphosphate synthase, which competes for geranylgeranyl diphosphate substrate and partially re-channels the biosynthetic pathway from carotenes back to gibberellins according to scheme shown in FIG. 1. Recovered level of gibberellins allows transgenic seeds to germinate.

What is claimed is:

1. A recoverable block of function (RBF) system for controlling segregation of transgene in plants, said RBF-system consisting of:
   one or more blocking constructs (BCs) each comprising a blocking gene capable of blocking germination;
      at least one of the blocking genes comprising a nucleotide sequence encoding phytoene synthase, expression of which prevents germination of seeds of the transgenic plants;
      and at least one of the blocking genes being operably linked to a promoter comprising repressor-binding sequence;
   a transgene of interest flanking at least one BC; and
      means for recovering the blocked germination, said means comprising at least one recovering construct (RC), said RC comprising repressor-encoding sequences under control of an inducible promoter.

2. The RBF-system according to claim 1, wherein at least one blocking gene is an unmodified crtB gene or a modified crtB gene.

3. The RBF-system according to claim 1, wherein the nucleotide sequence encoding phytoene synthase is expressing under the control of a germination specific promoter.

4. The RBF-system according to claim 3, wherein the germination specific promoter is a sulfhydryl (cysteine) endopeptidase (SH-EP) promoter, an amylase (AMY) promoter or a heat shock (HS) promoter.

5. The RBF-system according to claim 1, wherein means for recovering the blocked germination further comprises contacting said seeds with a composition comprising the combination of an effective amount of gibberellin or gibberellic acid; and carbohydrate.

6. The RBF-system according to claim 1, wherein
   the system comprises a first and a second BC,
   the first BC comprising a first blocking gene, said first blocking gene being crtB, and
   the second BC comprising a second blocking gene, said second blocking gene being barnase; and
   the transgene of interest being inserted in between of the first and the second BC.

7. The RBF-system according to claim 1, wherein recovering construct (RC) further comprises a recovering gene encoding an enzyme involved in biosynthetic pathway of a metabolite said metabolite depleted by overexpression of phytoene synthase.

8. The RBF-system according to claim 7, wherein the recovering gene encodes ent-copalyl diphosphate synthase or ent-kaurene synthase.

9. A recoverable block of function (RBF) system for controlling segregation of transgene in plants, said RBF-system consisting of:
   one or more blocking constructs (BCs) comprising a blocking gene capable of blocking germination,
      at least one of the blocking genes comprising a nucleotide sequence encoding phytoene synthase, expression of which prevents germination of seeds of the transgenic plants;
   a transgene of interest flanking at least one BC; and
   means for recovering the blocked germination, wherein means for recovering the blocked germination comprises contacting said seeds with a composition comprising the combination of an effective amount of gibberellin or gibberellic acid; and carbohydrate.

* * * * *

SEQUENCE LISTING

<160> NUMBER OF SEQ ID NOS: 20

<210> SEQ ID NO 1
<211> LENGTH: 891
<212> TYPE: DNA
<213> ORGANISM: artificial
<220> FEATURE:
<223> OTHER INFORMATION: Erwinia uredovora
<220> FEATURE:
<221> NAME/KEY: misc_feature
<222> LOCATION: (1)..(891)
<223> OTHER INFORMATION: crtB coding sequence

<400> SEQUENCE: 1

```
atggctgttg gctcgaaaag ttttgcgact gcctcaaagt tatttgatgc aaaaacccgg      60
cgcagcgtac tgatgctcta cgcctggtgc cgccattgtg acgatgttat tgacgatcag     120
acgctgggct tcaggcccg gcagcctgcc ttacaaacgc ccgaacaacg tctgatgcaa      180
cttgagatga aaacgcgcca ggcctatgca ggatcgcaga tgcacgaacc ggcgtttgcg     240
gcttttcagg aagtggctat ggctcatgat atcgccccgg cttacgcgtt tgatcatctg     300
gaaggcttcg ccatggatgt acgcgaagcg caatacagcc aactggatga tacgctgcgc     360
tattgctatc acgttgcagg cgttgtcggc ttgatgatgg cgcaaatcat gggcgtgcgg     420
gataacgcca cgctggaccg cgcctgtgac cttgggctgg catttcagtt gaccaatatt     480
gctcgcgata ttgtggacga tgcgcatgcg gccgctgtt atctgccggc aagctggctg     540
gagcatgaag gtctgaacaa agagaattat gcggcacctg aaaaccgtca ggcgctgagc     600
cgtatcgccc gtcgtttggt gcaggaagca gaaccttact atttgtctgc cacagccggc     660
ctggcagggt tgccctgcg ttccgcctgg gcaatcgcta cggcgaagca ggtttaccgg     720
aaaataggtg tcaaagttga acaggccggt cagcaagcct gggatcagcg gcagtcaacg     780
accacgcccg aaaaattaac gctgctgctg gccgctctg gtcaggccct tacttcccgg     840
atgcgggctc atcctccccg ccctgcccat ctctggcagc gcccgattta g              891
```

<210> SEQ ID NO 2
<211> LENGTH: 59
<212> TYPE: DNA
<213> ORGANISM: artificial
<220> FEATURE:
<223> OTHER INFORMATION: crtB.F1 cloning primer

<400> SEQUENCE: 2

```
atgaagctta tccatggatc gtctcacatg gctgttggct cgaaaagttt tgcgactgc        59
```

<210> SEQ ID NO 3
<211> LENGTH: 60
<212> TYPE: DNA
<213> ORGANISM: artificial
<220> FEATURE:
<223> OTHER INFORMATION: CrtB.R1 cloning primer

<400> SEQUENCE: 3

```
catggatcca tgctagcatg agctcgacta aatcgggcgc tgccagagat gggcagggcg       60
```

<210> SEQ ID NO 4
<211> LENGTH: 210
<212> TYPE: DNA
<213> ORGANISM: artificial
<220> FEATURE:
<223> OTHER INFORMATION: Pisum sp

```
<220> FEATURE:
<221> NAME/KEY: misc_feature
<222> LOCATION: (1)..(210)
<223> OTHER INFORMATION: DNA sequence coding for tps leader transit
      peptide

<400> SEQUENCE: 4
atggcttcta tgatatcctc ttccgctgtg acaacagtca gccgtgcctc tagggggcaa      60
tccgccgcag tggctccatt cggcggcctc aaatccatga ctggattccc agtgaagaag     120
gtcaacactg acattacttc cattacaagc aatggtggaa gagtaaagtg catgaacaac     180
ccttctcttc ttaaccatgc tgttgagacc                                      210

<210> SEQ ID NO 5
<211> LENGTH: 61
<212> TYPE: DNA
<213> ORGANISM: artificial
<220> FEATURE:
<223> OTHER INFORMATION: Tps.F1 cloning primer

<400> SEQUENCE: 5
aatccgccgc agtggctcca ttcggcggcc tcaaatccat gactggattc ccagtgaaga      60
a                                                                     61

<210> SEQ ID NO 6
<211> LENGTH: 64
<212> TYPE: DNA
<213> ORGANISM: artificial
<220> FEATURE:
<223> OTHER INFORMATION: Tps.R1 cloning primer

<400> SEQUENCE: 6
ccaccattgc ttgtaatgga agtaatgtca gtgttgacct tcttcactgg gaatccagtc      60
atgg                                                                  64

<210> SEQ ID NO 7
<211> LENGTH: 63
<212> TYPE: DNA
<213> ORGANISM: artificial
<220> FEATURE:
<223> OTHER INFORMATION: Tps.F2 cloning primer

<400> SEQUENCE: 7
atatcctctt ccgctgtgac aacagtcagc cgtgcctcta gggggcaatc cgccgcagtg      60
gct                                                                   63

<210> SEQ ID NO 8
<211> LENGTH: 51
<212> TYPE: DNA
<213> ORGANISM: artificial
<220> FEATURE:
<223> OTHER INFORMATION: Tps.R2 cloning primer

<400> SEQUENCE: 8
gaagagaagg gttgttcatg cactttactc ttccaccatt gcttgtaatg g              51

<210> SEQ ID NO 9
<211> LENGTH: 53
<212> TYPE: DNA
<213> ORGANISM: artificial
<220> FEATURE:
<223> OTHER INFORMATION: Tps.F3 cloning primer

<400> SEQUENCE: 9
```
gctatctaga gcgccatggc ttctatgata tcctcttccg ctgtgacaac agt    53

<210> SEQ ID NO 10
<211> LENGTH: 55
<212> TYPE: DNA
<213> ORGANISM: Artificial
<220> FEATURE:
<223> OTHER INFORMATION: Tps.R3 cloning primer

<400> SEQUENCE: 10
cgatggatcc gcgccatggt ctcaacagca tggttaagaa gagaagggtt gttca    55

<210> SEQ ID NO 11
<211> LENGTH: 1927
<212> TYPE: DNA
<213> ORGANISM: artificial
<220> FEATURE:
<223> OTHER INFORMATION: Vigna mungo
<220> FEATURE:
<221> NAME/KEY: misc_feature
<222> LOCATION: (1)..(1927)
<223> OTHER INFORMATION: SH-EP promoter
<220> FEATURE:
<221> NAME/KEY: misc_feature
<222> LOCATION: (1674)..(1927)
<223> OTHER INFORMATION: nos polyadenylation site

<400> SEQUENCE: 11
gagcttaact tttgaggcag agcttgtaaa ttgtaacagg tgaggtagaa agacggaaag    60
tacttttaat aataaaaggt tgaaaaatt aagaaaagaa gaagaaaata ttttgtgagt    120
gcacgcgatg gatctaatcc ttccatgaaa agaatatca agaataacaa aaattgacaa    180
aatcagcgaa tacttcaccc aaaagtctac acaataataa atgctaaatc acatataatt    240
tgtgatgcat aacgcattac gctatcgtaa tcctttacaa caagcaagaa cgtcatccca    300
gaatctcaac tcaaatcaaa accgttcatt cataaataaa aatattctt acattctttt    360 gcaaatagaa cctttgccaa attgaaataa caaactctag gtatttgtca aattaactta    420
ccaacttctc gttatataat tttagattta taatcatgtc tataaattat ttctatacac    480
tctctctcaa atttgacctt tacattctgt gatttatttg aacagaataa atcactgtaa    540
aactaaacaa ctctttaaaa aaggtaaatt aggaaaagtc gaaatcaata aattataaat    600
caatccctag aaaactgcaa gataatattc ttaccaaaat catttaaata aatttgtaag    660 tttttttcttt ataccaattt tctgagaccc agagacattc ttaaattcat aacaacggtt    720
ttaagtatca gagtataaca tctttgtata aatagatttt tgaacgttca ataactaaca    780
cgtcagtttt tgtttccacg ttgtacgttt aataacaata aatgcgtgag ttagattact    840
aatcagaagt tagaagtgta caagactaac tttatacaga aatatattgt ttcagactgc    900
actttatggt gcgtagcacc tcaaaactct tacctttcgc atacattttc acacttcatc    960
caaacctttc gaaaagtcac ttcccttata ttaaaggact atgatataaa aaagactata    1020
tgtgttacta atttattggt ttgtatattt gtaataaatc gttccatcaa gaggagctat    1080
cacatattga gaacagtaaa aaaaaaaaaa agttggtaaa aaaacatttt cttatattat    1140
atcataaaat cagttaccat agtattttag agttttcaga ataatgcttc acccaacttg    1200
caactcattg tgcctcaaaa caggacgtaa ccatgttact cactctcctg cacaacccct    1260
tgttaaactg atagcgtgat cagcatgcaa gagaaagatg attcttgaag catacgataa    1320
cagattgaat gtgacaaaaa gtttgtgtct cagcttcagg gtcggcacct aatacaaaag    1380

```
gaaaatttgt caggtttcct tccgtagttt cattcactat tattgaatcc tttggctacc    1440
attcttgaga aacacaaaca cttcttatat ctgttctaca caattctctg agtgcgtgcc    1500
acagtttggt atcttcatga ttgctcattg ttcatgccca taaggaacat gtaacttcct    1560
catttattta ttattgcttt tgttttcttc tcactagtta acttcgtttt ccctatataa    1620
accctccttt gttcccttcc cttcccatct tccatttatt gattccaaac acaatcgttc    1680
aaacatttgg caataaagtt tcttaagatt gaatcctgtt gccggtcttg cgatgattat    1740
catataattt ctgttgaatt acgttaagca tgtaataatt aacatgtaat gcatgacgtt    1800
atttatgaga tgggttttta tgattagagt cccgcaatta tacatttaat acgcgataga    1860
aaacaaaata tagcgcgcaa actaggataa attatcgcgc gcggtgtcat ctatgttact    1920
agatcga                                                              1927
```

<210> SEQ ID NO 12
<211> LENGTH: 336
<212> TYPE: DNA
<213> ORGANISM: artificial
<220> FEATURE:
<223> OTHER INFORMATION: Bacillus amyloliquefaciens
<220> FEATURE:
<221> NAME/KEY: misc_feature
<222> LOCATION: (1)..(336)
<223> OTHER INFORMATION: Barnase 1 synthetic coding sequence

<400> SEQUENCE: 12

```
atggcacaag ttatcaacac ctttgatgga gttgctgact accttcagac ctaccataaa     60
cttccagata actacatcac caagtctgag gctcaggctc ttggatgggt tgcttctaag    120
ggaaaccttg ctgatgtcgc tccaggaaag tctatcggag tgatatctt ctctaacagg     180 gagggaaagt tgccaggaaa gtctggaagg acctggaggg aggctgatat caactacacc    240
tctggattca ggaactctga tagaatcctt tactcttccg actggcttat ctacaagacc    300
actgaccact accagacctt caccaagatc cggtga                              336
```

<210> SEQ ID NO 13
<211> LENGTH: 336
<212> TYPE: DNA
<213> ORGANISM: artificial
<220> FEATURE:
<223> OTHER INFORMATION: Bacillus amyloliquefaciens
<220> FEATURE:
<221> NAME/KEY: misc_feature
<222> LOCATION: (1)..(336)
<223> OTHER INFORMATION: barnase 2 synthetic coding sequence

<400> SEQUENCE: 13

```
atggctcaag ttattaatac ttttgatgga gttgctgatt atcttcaaac ttatcataaa     60
cttccagata attatattac taaatctgaa gctcaagctc ttggatgggt tgcttctaaa    120
ggaaatcttg ctgatgttgc tccaggaaaa tctattggag gagatatttt ttcaaataga    180
gaaggaaaac ttccaggaaa atctggaaga acatggagag aagctgatat taattatact    240
tctggattta gaaattcaga tagaattctt tattcatctg attggcttat ttataaaact    300
acagatcatt atcaaacttt tacaaaaatt agataa                              336
```

<210> SEQ ID NO 14
<211> LENGTH: 1183
<212> TYPE: DNA
<213> ORGANISM: artificial
<220> FEATURE:
<223> OTHER INFORMATION: Brassica napus -continued

```
<220> FEATURE:
<221> NAME/KEY: misc_feature
<222> LOCATION: (1)..(1183)
<223> OTHER INFORMATION: CRU promoter with artificial polyadenylation
      site

<400> SEQUENCE: 14
cttctacacg ttttgaaaag ttaacctgtt ggttaaatgg ttagctatga ctctcgcaac      60
aaacccaacc cttaagatga tgatggttta acatttgaca acatagttaa gactgtgtct     120
atataatagt caacaaattc agattgtagt attatggagt caacatattt cgagatcaaa     180
aacattcaaa acgtaaatct atcgacgtct cacatagttt tgttatgaag ctgatgaaaa     240
aagttggaag acatagtttt gcaaacatca tttgttgcta acgtataaac gttggtttga     300
ttaaatgtaa taggataagg atatccgttt gttcatataa ttgagttaaa ttatattttg     360
gttattataa tatgttaagt tgaaaataaa taggtccaac aaccttgttt aaatagattt     420
tttaggagtg attcccttt aatagtatag attatactct cttcctaatc gaccttccgt      480
ggggtaaagt ggtcaattat attctttatg gatgagcttg attgagaatg ggtttatggg     540
ttatgacaag ggcatgtaca aatgtcactg cctcttgaca tgcaaccgaa cagttggcga     600
ctcaagtcgc agaagataca acggaccaaa ccctccgagt gtcgccgcgt ctgttatgtg     660
tcaccttttt gtctccttc cttaaaaatt ggtaactcat ttttcaaaaa aagaagagga     720
tagttttggc tgtatctcct aaactattcg atcacaacgc cagatatttt aatactggat     780
actagtgatg taatttgatt tgttaattgt caaaaagtag attctcctat ctcgtttta     840 gttcaattat tatatggtta aatgaattta agtcgattag aaatgattag ttaatcaacc     900
agagttgctc tataagtcta tactgataac atgaaccatt ttctaaaaat gagatagata     960
catttgaatt ttgtcgtggt ttggagtatg cggagatagt cgtacgcgca tgaacatcat    1020
gagacacttg cttcagctca cagagtgacg tgtaaagacc atagacccac gacttcatgc    1080
aaacccattc ctacgtggca caaaccttca tgctcactcc acatatataa actcctacca    1140
agtctccatg tttcttcatc catctatcac aaaaacacac aaa                      1183

<210> SEQ ID NO 15
<211> LENGTH: 7
<212> TYPE: DNA
<213> ORGANISM: artificial
<220> FEATURE:
<223> OTHER INFORMATION: chemically synthetized
<220> FEATURE:
<221> NAME/KEY: misc_feature
<222> LOCATION: (1)..(7)
<223> OTHER INFORMATION: TATA- box

<400> SEQUENCE: 15 tatataa                                                                7

<210> SEQ ID NO 16
<211> LENGTH: 1659
<212> TYPE: DNA
<213> ORGANISM: artificial
<220> FEATURE:
<223> OTHER INFORMATION: Vigna mungo
<220> FEATURE:
<221> NAME/KEY: misc_feature
<222> LOCATION: (1)..(1659)
<223> OTHER INFORMATION: modified SHEP promoter with three tet operators
      in the vicinity of the TATA box
<220> FEATURE:
<221> NAME/KEY: misc_feature
<222> LOCATION: (1591)..(1609)
```

```
<223> OTHER INFORMATION: Tet operator
<220> FEATURE:
<221> NAME/KEY: misc_feature
<222> LOCATION: (1611)..(1617)
<223> OTHER INFORMATION: TATA-box
<220> FEATURE:
<221> NAME/KEY: misc_feature
<222> LOCATION: (1620)..(1638)
<223> OTHER INFORMATION: Tet operator
<220> FEATURE:
<221> NAME/KEY: misc_feature
<222> LOCATION: (1641)..(1659)
<223> OTHER INFORMATION: Tet operator

<400> SEQUENCE: 16
cttaactttt gaggcagagc ttgtaaattg taacaggtga ggtagaaaga cggaaagtac        60
ttttaataat aaaaggtttg aaaaattaag aaaagaagaa gaaatatttt tgtgagtgca       120
cgcgatggat ctaatccttc catgaaaaag aatatcaaga ataacaaaaa ttgacaaaat       180
cagcgaatac ttcacccaaa agtctacaca ataataaatg ctaaatcaca tataatttgt       240
gatgcataac gcattacgct atcgtaatcc tttacaacaa gcaagaacgt catcccagaa       300
tctcaactca aatcaaaacc gttcattcat aaataaaaaa tattcttaca ttcttttgca       360
aatagaacct tgccaaaatt gaaataacaa actctaggta tttgtcaaat taacttacca       420
acttctcgtt atataatttt agattttaaa tcatgtctat aaattatttc tatacactct       480
ctctcaaatt tgacctttac attctgtgat ttatttgaac agaataaatc actgtaaaac       540
taaacaactc tttaaaaaag gtaaattagg aaaagtcgaa atcaataaat tataaatcaa       600
tccctagaaa actgcaagat aatattctta ccaaaatcat ttaaataaat ttgtaagttt       660
tttctttata ccaattttct gagacccaga gacattctta aattcataac aacggtttta       720
agtatcagag tataacatct ttgtataaat agattttttga acgttcaata actaacacgt       780
cagttttttgt ttccacgttg tacgtttaat aacaataaat gcgtgagtta gattactaat       840
cagaagttag aagtgtacaa gactaacttt atacagaaat atattgtttc agactgcact       900
ttatggtgcg tagcacctca aaactcttac ctttcgcata cattttcaca cttcatccaa       960
acctttcgaa aagtcacttc ccttatatta aaggactatg atataaaaaa gactatatgt      1020
gttactaatt tattggtttg tatatttgta ataaatcgtt ccatcaagag gagctatcac      1080
atattgagaa cagtaaaaaa aaaaaaaagt tggtaaaaaa cattttctt atattatatc      1140
ataaaatcag ttaccatagt attttagagt tttcagaata atgcttcacc caacttgcaa      1200
ctcattgtgc ctcaaaacag gacgtaacca tgttactcac tctcctgcac aacccccttgt     1260
taaactgata gcgtgatcag catgcaagag aaagatgatt cttgaagcat acgataacag      1320
attgaatgtg acaaaaagtt tgtgtctcag cttcagggtc ggcacctaat acaaaaggaa      1380
aatttgtcag gtttccttcc gtagtttcat tcactattat tgaatccttt ggctaccatt      1440
cttgagaaac acaaacactt cttatatctg ttctacacaa ttctctgagt gcgtgccaca      1500
gtttggtatc ttcatgattg ctcattgttc atgcccataa ggaacatgta acttcctcat      1560
ttatttatta ttgcttttgt tttcttctca actctatcac tgatagagtc tatataaaca      1620
ctctatcact gatagagtga actctatcac tgatagagt                             1659

<210> SEQ ID NO 17
<211> LENGTH: 1293
<212> TYPE: DNA
<213> ORGANISM: artificial
<220> FEATURE:
<223> OTHER INFORMATION: Brassica napus
```

<220> FEATURE:
<221> NAME/KEY: misc_feature
<222> LOCATION: (1)..(1293)
<223> OTHER INFORMATION: modified CRU promoter with three tet operators
    in the vicinity of TATA box
<220> FEATURE:
<221> NAME/KEY: misc_feature
<222> LOCATION: (1226)..(1244)
<223> OTHER INFORMATION: Tet operator
<220> FEATURE:
<221> NAME/KEY: misc_feature
<222> LOCATION: (1246)..(1252)
<223> OTHER INFORMATION: TATA-box
<220> FEATURE:
<221> NAME/KEY: misc_feature
<222> LOCATION: (1254)..(1272)
<223> OTHER INFORMATION: Tet operator
<220> FEATURE:
<221> NAME/KEY: misc_feature
<222> LOCATION: (1275)..(1293)
<223> OTHER INFORMATION: Tet operator

<400> SEQUENCE: 17

```
cttctacacg ttttgaaaag ttaacctgtt ggttaaatgg ttagctatga ctctcgcaac      60
aaacccaacc cttaagatga tgatggttta acatttgaca acatagttaa gactgtgtct    120
atataatagt caacaaattc agattgtagt attatggagt caacatattt cgagatcaaa    180
aacattcaaa acgtaaatct atcgacgtct cacatagttt tgttatgaag ctgatgaaaa    240
aagttggaag acatagtttt gcaaacatca tttgttgcta acgtataaac gttggtttga    300
ttaaatgtaa taggataagg atatccgttt gttcatataa ttgagttaaa ttatattttg    360
gttattataa tatgttaagt tgaaaataaa taggtccaac aaccttgttt aaatagattt    420
tttaggagtg attcccttttt aatagtatag attatactct cttcctaatc gaccttccgt    480
ggggtaaagt ggtcaattat attctttatg gatgagcttg attgagaatg ggtttatggg    540
ttatgacaag ggcatgtaca aatgtcactg cctcttgaca tgcaaccgaa cagttggcga    600
ctcaagtcgc agaagataca acggaccaaa ccctccgagt gtcgccgcgt ctgttatgtg    660
tcacctttt gtctcctttc cttaaaaatt ggtaactcat ttttcaaaaa aagaagagga    720
tagttttggc tgtatctcct aaactattcg atcacaacgc cagatatttt aatactggat    780
actagtgatg taatttgatt tgttaattgt caaaaagtag attctcctat ctcgttttta    840
gttcaattat tatatggtta aatgaattta agtcgattag aaatgattag ttaatcaacc    900
agagttgctc tataagtcta tactgataac atgaaccatt ttctaaaaat gagatagata    960
catttgaatt ttgtcgtggt ttggagtatg cggagatagt cgtacgcgca tgaacatcat   1020
gagacacttg cttcagctca cagagtgacg tgtaaagacc atagacccac gacttcatgc   1080
aaacccattc ctacgtggca caaaccttca tgctcactcc acatatataa actcctacca   1140
agtctccatg tttcttcatc catctatcac aaaaacacac aaatagaccc acgacttcat   1200
gcaaacccat tcctacgtgg cacaaactct atcactgata gagtctatat aagactctat   1260
cactgataga gtgaactcta tcactgatag agt                                 1293
```

<210> SEQ ID NO 18
<211> LENGTH: 19
<212> TYPE: DNA
<213> ORGANISM: artificial
<220> FEATURE:
<223> OTHER INFORMATION: chemically syntetized
<220> FEATURE:
<221> NAME/KEY: misc_feature
<222> LOCATION: (1)..(19)
<223> OTHER INFORMATION: tet operator

```
<220> FEATURE:
<221> NAME/KEY: misc_feature
<222> LOCATION: (1)..(19)
<223> OTHER INFORMATION: Tet operator

<400> SEQUENCE: 18
actctatcac tgatagagt                                                    19

<210> SEQ ID NO 19
<211> LENGTH: 624
<212> TYPE: DNA
<213> ORGANISM: artificial
<220> FEATURE:
<223> OTHER INFORMATION: E.coli transposon Tn10
<220> FEATURE:
<221> NAME/KEY: misc_feature
<222> LOCATION: (1)..(624)
<223> OTHER INFORMATION: TetR gene

<400> SEQUENCE: 19
atgtccagat tagataaaag taaagtgatt aacagcgcat tagagctgct taatgaggtc        60
ggaatcgaag gtttaacaac ccgtaaactc gcccagaagc taggtgtaga gcagcctaca       120
ttgtattggc atgtaaaaaa taagcgggct ttgctcgacg ccttagccat tgagatgtta       180
gataggcacc atactcactt tgccccttta aaggggaaa gctggcaaga ttttttacgt        240
aataacgcta aaagttttag atgtgcttta ctaagtcatc gcgatggagc aaaagtacat       300
ttaggtacac ggcctacaga aaacagtat gaaactctcg aaaatcaatt agccttttta       360
tgccaacaag gttttttcact agagaatgca ttatatgcac tcagcgctgt ggggcatttt    420
actttaggtt gcgtattgga agatcaagag catcaagtcg ctaaagaaga aagggaaaca      480
cctactactg atagtatgcc gccattatta cgacaagcta tcgaattatt tgatcaccaa     540
ggtgcagagc cagccttctt attcggcctt gaattgatca tatgcggatt agaaaaacaa    600
cttaaatgtg aaagtgggtc ttaa                                              624

<210> SEQ ID NO 20
<211> LENGTH: 299
<212> TYPE: DNA
<213> ORGANISM: artificial
<220> FEATURE:
<223> OTHER INFORMATION: Bacillus amyloliquefaciens
<220> FEATURE:
<221> NAME/KEY: misc_feature
<222> LOCATION: (1)..(299)
<223> OTHER INFORMATION: plant adapted synthetic coding sequence of
      Barstar gene

<400> SEQUENCE: 20
cgcggatcct gatcatgaag aaggctgtta tcaacggtga gcaaattagg tctatctctg        60
atcttcacca gacccttaag aaggagcttg ctcttccaga gtactacgga gagaaccttg      120
atgctctatg ggattgcctt accggatggg tggagtaccc acttgttttg gagtggaggc      180
agtttgagca gtctaagcag cttactgaga atggagctga gagtgttctt caggttttcc      240
gggaggctaa ggctgaggga tgcgatatca ccatcattct ttcttgagag ctcgagcgc       299
```